(12) United States Patent
Pond

(10) Patent No.: US 11,503,851 B1
(45) Date of Patent: *Nov. 22, 2022

(54) COMPOSITIONS AND METHODS TO COUNTERACT PROCESSES ASSOCIATED WITH INFLAMMATION AND SENESCENCE AND TO SUPPORT CELLULAR ENERGY AND/OR METABOLISM

(71) Applicant: DailyColors Health Inc., Sebastopol, CA (US)

(72) Inventor: Hartley Pond, Sebastopol, CA (US)

(73) Assignee: DailyColors Health, Inc., Sebastopol, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/843,140

(22) Filed: Jun. 17, 2022

Related U.S. Application Data

(60) Provisional application No. 63/285,591, filed on Dec. 3, 2021, provisional application No. 63/215,716, filed on Jun. 28, 2021.

(51) Int. Cl.
*A23L 33/105* (2016.01)
*A23L 33/135* (2016.01)
(Continued)

(52) U.S. Cl.
CPC ........... *A23L 33/105* (2016.08); *A23L 33/135* (2016.08); *A23L 33/15* (2016.08); *A23L 33/40* (2016.08)

(58) Field of Classification Search
None
See application file for complete search history.

(56) References Cited

U.S. PATENT DOCUMENTS

| 2015/0190450 A1* | 7/2015 | Chang | A61K 8/987 |
| | | | 424/59 |
| 2018/0078649 A1* | 3/2018 | Zu | C12N 15/117 |
| 2018/0318323 A1 | 11/2018 | Roman et al. | |

FOREIGN PATENT DOCUMENTS

| CN | 108541953 A | 9/2018 |
| KR | 1020090078939 A | 7/2009 |

(Continued)

OTHER PUBLICATIONS

Ahmad et al., "Assessment of Risk Factors and Biomarkers Associated With Risk of Cardiovascular Disease Among Women Consuming a Mediterranean Diet," Dec. 7, 2018; 1(8); 14 pgs.

(Continued)

*Primary Examiner* — Patricia A George
(74) *Attorney, Agent, or Firm* — Martin Fessenmaier; Umberg Zipser LLP

(57) ABSTRACT

Contemplated compositions and methods are based on a combination of polyphenols commonly found in the Mediterranean diet that, when combined, reduce pro-inflammatory signaling and expression of senescence-associated genes and support mitochondrial biogenesis and cellular energy metabolism. Notably, the observed pleiotropic effects did not only span across multiple signaling pathways, but also exhibited synergistic activity with respect to a number of markers associated with reduction of age-related decline in energy, immunity, and increase or persistence of chronic subacute inflammation. Viewed from a different perspective, contemplated compositions represent a symphony of biochemically diverse molecules that form the foundation for numerous benefits typically observed with the Mediterranean diet.

18 Claims, 26 Drawing Sheets

(51) Int. Cl.
  *A23L 33/15*  (2016.01)
  *A23L 33/00*  (2016.01)

(56) References Cited

FOREIGN PATENT DOCUMENTS

| KR | 1020180020718 A | 2/2018 |
|---|---|---|
| WO | 2019092896 A1 | 5/2019 |

OTHER PUBLICATIONS

Allard et al., "The ectonucleotidases CD39 and CD73: novel checkpoint inhibitor targets," Immunol Rev., Mar. 2017; 276(1):121-144.
Anhe et al., "Triggering Akkermansia with dietary polyphenols: A new weapon to combat the metabolic syndrome?" Gut Microbes, 2016; 7(2):146-153.
Antonioli et al., "CD39 and CD73 in immunity and inflammation," Trends Mol Med., Jun. 2013; 19(6):355-367.
Arora et al., "Combinatorial Epigenetics Impact of Polyphenols and Phytochemicals in Cancer Prevention and Therapy," International Journal of Molecular Sciences, 2019; 20:4567; 42 pgs.
Beecher, Gary R., "Overview of Dietary Flavonoids: Nomenclature, Occurrence and Intake," The Journal of Nutrition, Oct. 2003; 133(10):3248S-3254S.
Biagi et al., "Gut Microbiota and Extreme Longevity," Current Biology, Jun. 6, 2016; 26:1480-1485.
Billingsley et al., "The antioxidant potential of Mediterranean diet in patients at high cardiovascular risk: an in-depth review of the PREDIMED," Nutrition and Diabetes, 2018; 8:13; 8 pgs.
Bose et al., "Targeting the JAK/STAT Signaling Pathway Using Phytocompounds for Cancer Prevention and Therapy," Cells, 2020; 9,1451; 40 pgs.
Caldwell et al., "Arginase: A Multifaceted Enzyme Important in Health and Disease," Physiol. Rev., 2018; 98:641-665.
Cham et al., "Immunotherapeutic Blockade of CD47 Inhibitory Signaling Enhances Innate and Adaptive Immune Responses to Viral Infection," Cell Reports, 2020; 31, 107494; 14 pgs.
Chini et al., "The NADase CD38 is induced by factors secreted from senescent cells providing a potential link between senescence and age-related cellular NAD+ decline," Biochem Biophys Res Commun., May 28, 2019; 513(2):486-493.
Chini et al., "The Pharamacology of CD38/NADase: An emerging target for cancer and aging diseases," Trends Pharmacol Sci., Apr. 2018; 39(4):424-436.
Crooke et al., "Low expression of CD39 and CD73 genes in centenarians compared with octogenarians," Immunity & Ageing; 2017; 14:11; 5 pgs.
Fytexia, OXXYNEA Information Sheet, retrieved from the internet on Oct. 24, 2019, 4 pgs. www.fytexia.com—www.oxxynea.com.
Gomez-Pinilla et al., "Natural mood foods: The actions of polyphenols against psychiatric and cognitive disorders," May 2012; 15(3):127-133.
Goncalves et al., "Chapter 6: Phenolic Compounds—Biological Activity: Inhibitory Properties of Phenolic Compounds Against Enzymes Linked with Human Diseases," Intech Open Science, 2017, pp. 99-118.
Gonzalez de Mejia et al., "The Colors of Health: Chemistry, Bioactivity, and Market Demand for Colorful Foods and Matural Food Sources of Colorants," Annu Rev. Food Sci. Technol., 2020; 15:47; 11:10.1-10.38.
Gu et al., "Mediterranean Diet, Inflammatory and Metabolic Biomarkers, and Risk of Alzheimer's Disease," J Alzheimers Dis., 2010; 22(2):483-492.
Hogan et al., "The Multi-faceted Ecto-enzyme CD38: Roles in Immunomodulation, Cancer, Aging, and Metabolic Diseases," Frontiers in Immunology, May 2019; 10, Art. 1187; 12 pgs.
Huang et al., "Curcumin inhibits BACE1 expression through the interaction between ERBeta and NFkB signaling pathway in SH-SY5Y cells," Molecular and Cellular Biochemistry, 2020; 463:161-173.
Jobs, et al., "Association Between Serum Cathepsin S and Mortality in Older Adults," JAMA, Sep. 14, 2011; 306(10):1113-1121.
Koelsch, Gerald, "BACE1 Function and Inhibition: Implications of Intervention in the Amyloid Pathway of Alzheimer's Disease Pathology," Molecules, 2017; 22, 1723; 20 pgs.
Lahoz et al., "Relationship of the Adherence to a Mediterranean Diet and Its Main Components with CRP Levels in the Spanish Population," Nutrients, 2018; 10, 379; 9 pgs.
Lakey-Beitia et al., "Polyphenols as Therapeutic Molecules in Alzheimer's Disease, Through Modulating Amyloid Pathways" Mol. Neurobiol., 2015; 51:466-479.
Marttila et al., "Aging-associated increase in indoleamine 2,3-dioxygenase (IDO) activity appears to be unrelated to the transcription of the IDO1 or IDO2 genes in peripheral blood mononuclear cells," Immunity & Ageing, 2011; 8:9; 4 pgs.
Masi et al., "Aging Modulates the Influence of Arginase on Endothelial Dysfunction in Obesity," Arterioscler Thromb Vasc Biol, 2018; 38:2474-2483.
Mushtaq et al., "Neuroprotective Mechanisms Mediated by CDK5 Inhibition," Curr Pharm Des., 2016; 22(5):527-534.
PCT International Search Report and Written Opinion, International Application No. PCT/US2021/016670, International filing date Feb. 4, 2021, 11 pages.
Prendergast et al., "Discovery of IDO1 inhibitors: from bench to bedside," Cancer Res., Dec. 15, 2017; 77(24):6795-6811.
Schwartz et al., "JAK inhibition as a therapeutic strategy for immune and inflammatory diseases," Nat Rev Drug Discov., Dec. 28, 2017; 17(1):78; 41 pgs.
Sreekumar, et al., "Pomegranate Fruit as a Rich Source of Biologically Active Compounds," BioMed Research International, 2014; 12 pgs.
Sureda et al., "Adherence to the Mediterranean Diet and Inflammatory Markers," Nutrients, Jan. 10, 2018; 10, 62; 13 pgs.
Xu et al., "Perspective: Targeting the JAK/STAT pathway to fight age-related dysfunction," Pharmacol Res., Sep. 2016; 111:152-154.
Zhao et al., "What Else Can CD39 Tell US?" Frontiers in Immunology, Jun. 2017; vol. 8; 10 pgs.

* cited by examiner

COMPOSITIONS AND METHODS TO COUNTERACT PROCESSES ASSOCIATED WITH INFLAMMATION AND SENESCENCE AND TO SUPPORT CELLULAR ENERGY AND/OR METABOLISM

This application claims priority to our copending U.S. Provisional Patent applications with the Ser. No. 63/215,716, filed Jun. 28, 2021, and 63/285,591, filed Dec. 3, 2021, both of which are incorporated by reference herein.

FIELD OF THE INVENTION

The field of the invention is compositions and methods for nutritional supplements, especially as it relates polyphenols and polyphenol mixtures and their use in reduction of various conditions associated with ageing, such as mild/chronic inflammation, age-related decline of immunity, decreased energy metabolism, and/or obesity.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

There is a considerable variety of vitamins and other isolated nutritional compounds, and alleged benefits of such compounds include, among numerous other effects, immune support, anti-inflammatory effects, anti-ageing effects, cardiac support, and digestive support. Unfortunately, there is only a rather small body of evidence that substantiates some aspects of these alleged benefits when these vitamins and other isolated nutritional compounds are ingested. Similarly, where the nutritional supplement is an extract or powdered form of a plant part, various benefits are advertised, but actual benefits are often poorly or even not at all proven. Moreover, isolated nutritional compounds as well as individual plant extracts and concentrates are generally not reflective of a healthy diet.

Notably, there are certain geographic and ethnographic diet types that are associated with overall health, longevity, and/or physical resilience, and such beneficial effects are indeed well documented and substantiated. For example, the Mediterranean diet is typically associated with lower cardiovascular risk factors (see e.g., Nutrients 2018, 10, 379; doi:10.3390/nu10030379), lower inflammatory and metabolic biomarkers, a reduction in risk of Alzheimer's disease (see e.g., J Alzheimers Dis. 2010; 22(2): 483-492), and with a redaction in certain inflammatory markers (see e.g., Nutrients 2018, 10, 62; doi:10.3390/nu10010062). One common ingredient class found in such diets are polyphenols, and various studies have been published regarding specific benefits of individual dietary polyphenols (see e.g., Inhibitory Properties of Phenolic Compounds Against Enzymes Linked with Human Diseases: URL:dx.doi.org/10.5772/66844), and selected colored polyphenols (see e.g., Annu. Rev. Food Sci. Technol. 2020. 11:10.1-10.38). However, due to the complexity and large number of chemically distinct polyphenols, many studies only focus on single polyphenols and particular biochemical effects of such compounds or provide general epidemiological information without more detailed molecular characterization of the diets.

In an effort to supplement a diet with multiple polyphenols, various supplements are known. For example, Vital Reds (by Gundry MD) provides a commercially available concentrated polyphenol powder blend from a number of red colored plant materials to increase energy and improve digestion. Such blend advantageously includes a variety of chemically distract polyphenols. However, the selection of plant materials used as a source of polyphenols is not reflective of common dietary intake. Similarly, Oxxynea by Fytexia, a commercially available mixture of grape, olive, pomegranate, green tea, grapefruit, bilberry, and orange extracts is offered as an antioxidant formulation to protect cells from oxidative stress (see e.g., Oxxynea by Fytexia). While beneficial to reduce oxidative stress, the source ingredients for such antioxidant formulations are typically not proven to affect molecular signatures associated with (chromic subacute) inflammation, NFκB signaling, decreased energy metabolism, senescence, age-related decline in immunity, and/or obesity.

Thus, even though various nutritional supplements are known in the art, all or almost all of them suffer from various disadvantages. Consequently, there is a need to provide improved compositions and methods for nutritional supplements, and especially those that are proven to counteract (chronic subacute) inflammation, NFκB signaling, decreased energy metabolism, senescence, age-related decline in immunity, and/or obesity.

SUMMARY OF THE INVENTION

The inventor has now discovered various compositions and methods for specific combinations of polyphenols and/or polyphenol-rich materials (e.g., extracts and powders) commonly found in food items of the Mediterranean diet that beneficially modulated various molecular signatures associated with age-related decline in immunity, inflammation, decreased energy metabolism and/or obesity. Consequently, the polyphenols and/or polyphenol-rich materials presented herein may be advantageously employed in a nutritionally-based approach to combat inflammaging, which can be characterized by one or more of an age-related decline in immunity, increased or chronic inflammation, decreased energy metabolism, and/or obesity.

In one aspect of the inventive subject matter, the inventor contemplates a nutritional composition that comprises a nutritionally acceptable carrier in combination with a plurality of chemically distinct polyphenol-containing plant materials having a red color, a green color, an orange-yellow color, and a purple-blue color, and in especially preferred embodiments, the red colored plant materials, the green colored plant materials, the orange-yellow colored plant materials, and the purple-blue colored plant materials are present in synergistic quantities with respect to reducing pro-inflammatory cytokine release in human leukocytes.

For example, the red colored plant materials may comprise an apple extract, a pomegranate extract, a tomato powder, and a beet root powder, the green colored plant materials may comprise an olive extract, a rosemary extract, a green coffee bean extract, and a kale powder, the orange-yellow colored plant materials may comprise an onion extract, a ginger extract, a grapefruit extract, and a carrot powder, and/or the purple-blue colored plant materials comprise a grape extract, a blueberry extract, a currant powder, and an elderberry powder. Viewed from a different perspective, the colored plant materials may be selected on the basis of or may be part of the Mediterranean diet.

In some embodiments, the pro-inflammatory cytokine release is release of at least one, or at least two, or at least three of a tumor necrosis factor alpha (TNF-alpha), interleukin-6 (IL-6), prostaglandin $E_2$ ($PGE_2$), and isoprostane. In other embodiments, the pro-inflammatory cytokine release is release of tumor necrosis factor alpha (TNF-alpha), interleukin-6 (IL-6), prostaglandin $E_2$ ($PGE_2$), and isoprostane.

It should still further be appreciated that the compositions presented herein may further reduce expression of NFκB, increase glucose uptake into a cell, increase mitochondrial biogenesis in a cell, reduce oxidative damage due to reactive oxygen species, reduce expression of pro-inflammatory adipokines, and/or reduce expression of one or more senescence associated genes.

Most typically, but not necessarily, the composition will be formulated for oral administration, either as bulk material or formulated in single dosage units. For example, a single dosage unit may contain between 50 and 1,000 mg of the composition, and may be formulated as a capsule, a gummy, or a bulk powder. As will also be readily appreciated, contemplated compositions may further include a vitamin, a dietary trace element or mineral, a probiotic, and/or a prebiotic. Similarly, contemplated compositions may also include a niacin, a niacinamide, a nicotinamide riboside, a nicotinamide mononucleotide, a nicotinamide adenine dinucleotide, and/or a nutritionally acceptable CD38 inhibitor.

Therefore, contemplated compositions are thought to be effective to treat or reduce a symptom associated with an inflammatory condition, a metabolic dysregulation, a neurological condition, a cardiovascular condition, senescence, and/or oxidative stress.

Consequently, the inventor contemplates a method of supporting health in a subject in which a composition as presented herein is administered to the individual. For example, the composition may be administered in an amount effective to thereby treat or reduce a symptom associated with an inflammatory condition, a metabolic dysregulation, a neurological condition, a cardiovascular condition, senescence, and/or oxidative stress. Therefore, administration may be over a period of at least 30 days and/or at a daily dose of between 50 and 1,000 mg. Thus, contemplated compositions may be used to support health and healthy ageing in a subject by oral administration of the composition.

In a further aspect of the inventive subject matter, the inventor therefore also contemplates a method of reducing inflammaging in a subject that includes a step of administering to the subject a nutritionally acceptable carrier in combination with a plurality of chemically distinct polyphenol-containing plant materials having a red color, a green color, an orange-yellow color, and a purple-blue color, wherein the combination of plant materials reduce release of at least one pro-inflammatory cytokine in human cells and reduce expression of at least one senescence-associated gene in human cells.

In certain embodiments, the red colored plant materials may comprise an apple extract, a pomegranate extract, a tomato powder, and a beet root powder, the green colored plant materials may comprise an olive extract, a rosemary extract, a green coffee bean extract, and a kale powder, the orange-yellow colored plant materials may comprise an onion extract, a ginger extract, a grapefruit extract, and a carrot powder, and/or the purple-blue colored plant materials may comprise a grape extract, a blueberry extract, a currant powder, and an elderberry powder. Thus, the red colored plant materials the green colored plant materials, the orange-yellow colored plant materials, and the purple-blue colored plant materials are part of or may be selected on the basis of a Mediterranean diet.

Most typically, the pro-inflammatory cytokine is selected from the group consisting of tumor necrosis factor alpha (TNF-alpha), interleukin-6 (IL-6), prostaglandin E2 (PGE2), and isoprostane. In especially preferred aspects, the red colored plant materials, the green colored plant materials, the orange-yellow colored plant materials, and the purple-blue colored plant materials will be present in synergistic quantities with respect to reducing pro-inflammatory cytokine release in the human cells. With respect to the senescence-associated gene it is contemplated that the senescence-associated gene may be selected from the group consisting of HGF, c-fos, p16INKL and p21.

Beneficially the reduction in inflammaging will comprise a reduction in age-related decline of immunity, a reduction in age-related decreased energy metabolism, a reduction in age-related decrease in mitochondrial biogenesis, a reduction in at least one symptom associated with inflammation, and/or a reduction in at least one symptom associated with metabolic syndrome.

Moreover, it should be appreciated that in at least some embodiments administration of the composition further advantageously reduces the expression of NFκB, increases glucose uptake into a cell, increases mitochondrial biogenesis in a cell, reduces oxidative damage due to reactive oxygen species, reduces expression of pro-inflammatory adipokines, and/or increases intracellular ATP.

Preferably, but not necessarily, administration to the subject comprises oral administration of the plurality of chemically distinct polyphenol-containing plant materials, for example, at a dosage of between about 50 and 1,000 mg. Where desired, the plurality of chemically distinct polyphenol-containing plant materials may be formulated as a tablet, a drink, or a gummy. Moreover, contemplated materials may additionally include a vitamin, a dietary trace element or mineral, a probiotic, and/or a prebiotic. Likewise, the combination of plant materials may additionally include a niacin, a niacinamide, a nicotinamide riboside, a nicotinamide mononucleotide, a nicotinamide adenine dinucleotide, and/or a nutritionally acceptable CD38 inhibitor.

In yet another aspect of the inventive subject matter, the inventor also contemplates a method of reducing inflammation in a subject that includes a step of administering to the subject a nutritionally acceptable carrier in combination with a plurality of chemically distinct polyphenol-containing plant materials having a red color, a green color, an orange-yellow color, and a purple-blue color. Preferably, the red colored plant materials comprise an apple extract, a pomegranate extract, a tomato powder, and a beet root powder, the green colored plant materials comprise an olive extract, a rosemary extract, a green coffee bean extract, and a kale powder, the orange-yellow colored plant materials comprise an onion extract, a ginger extract, a grapefruit extract, and a carrot powder, and the purple-blue colored plant materials comprise a grape extract, a blueberry extract, a currant powder, and an elderberry powder. In such methods, the combination of plant materials, upon administration, will reduce at least one pro-inflammatory cytokine, reduce NFκF signaling, and/or reduce at least one pro-inflammatory adipokine in the subject. Preferably, but not necessarily, the combination of plant materials is a synergistic combination with respect to the reduction of the at least one cytokine.

In still another aspect of the inventive subject matter, the inventor contemplates a method of increasing glucose uptake in a cell that includes a step of contacting the cell with a plurality of chemically distinct polyphenol-containing plant materials having a red color, a green color, an orange-yellow color, and a purple-blue color, wherein the red colored plant materials comprise an apple extract, a pomegranate extract, a tomato powder, and a beet root powder, wherein the green colored plant materials comprise an olive extract, a rosemary extract, a green coffee bean extract, and a kale powder, wherein the orange-yellow colored plant materials comprise an onion extract, a ginger extract, a grapefruit extract, and a carrot powder, and wherein the purple-blue colored plant materials comprise a grape extract, a blueberry extract, a currant powder, and an elderberry powder. In such methods, the combination of plant materials, upon contacting the cell, increases glucose uptake into the cell. Notably, and as described in more detail below, it was observed that the increased glucose uptake into the cell was similar or greater than an increased glucose uptake (under otherwise same conditions) using a thiazolinedione drug such as rosiglitazone.

In a further aspect of the inventive subject matter, the inventor also contemplates a method of increasing ATP levels in a cell that includes a step of contacting the cell with a plurality of chemically distinct polyphenol-containing plant materials having a red color, a green color, an orange-yellow color, and a purple-blue color, wherein the red colored plant materials comprise an apple extract, a pomegranate extract, a tomato powder, and a beet root powder, wherein the green colored plant materials comprise an olive extract, a rosemary extract, a green coffee bean extract, and a kale powder, wherein the orange-yellow colored plant materials comprise an onion extract, a ginger extract, a grapefruit extract, and a carrot powder, and wherein the purple-blue colored plant materials comprise a grape extract, a blueberry extract, a currant powder, and an elderberry powder. In such methods, the combination of plant materials, upon contacting the cell, increases ATP levels in the cell (and especially a muscle cell).

Therefore, and viewed from a different perspective, the inventor contemplates a plurality of chemically distinct polyphenol-containing plant materials having a red color, a green color, an orange-yellow color, and a purple-blue color for use in reduction of at least one symptom of inflammaging in an individual ingesting the plant material.

Similarly, the inventor also contemplates use of a nutritional composition as presented herein to reduce pro-inflammatory cytokine release in human leukocytes, reduce NFκB signaling, increase glucose uptake into a cell, increases mitochondrial biogenesis in a cell, reduce oxidative damage due to reactive oxygen species, reduce expression of pro-inflammatory adipokines, and/or reduce expression of at least one senescence associated gene.

Various objects, features, aspects, and advantages of the inventive subject matter will become more apparent from the following detailed description of preferred embodiments, along with the accompanying drawing figures in which like numerals represent like components.

DETAILED DESCRIPTION

Figure 1:
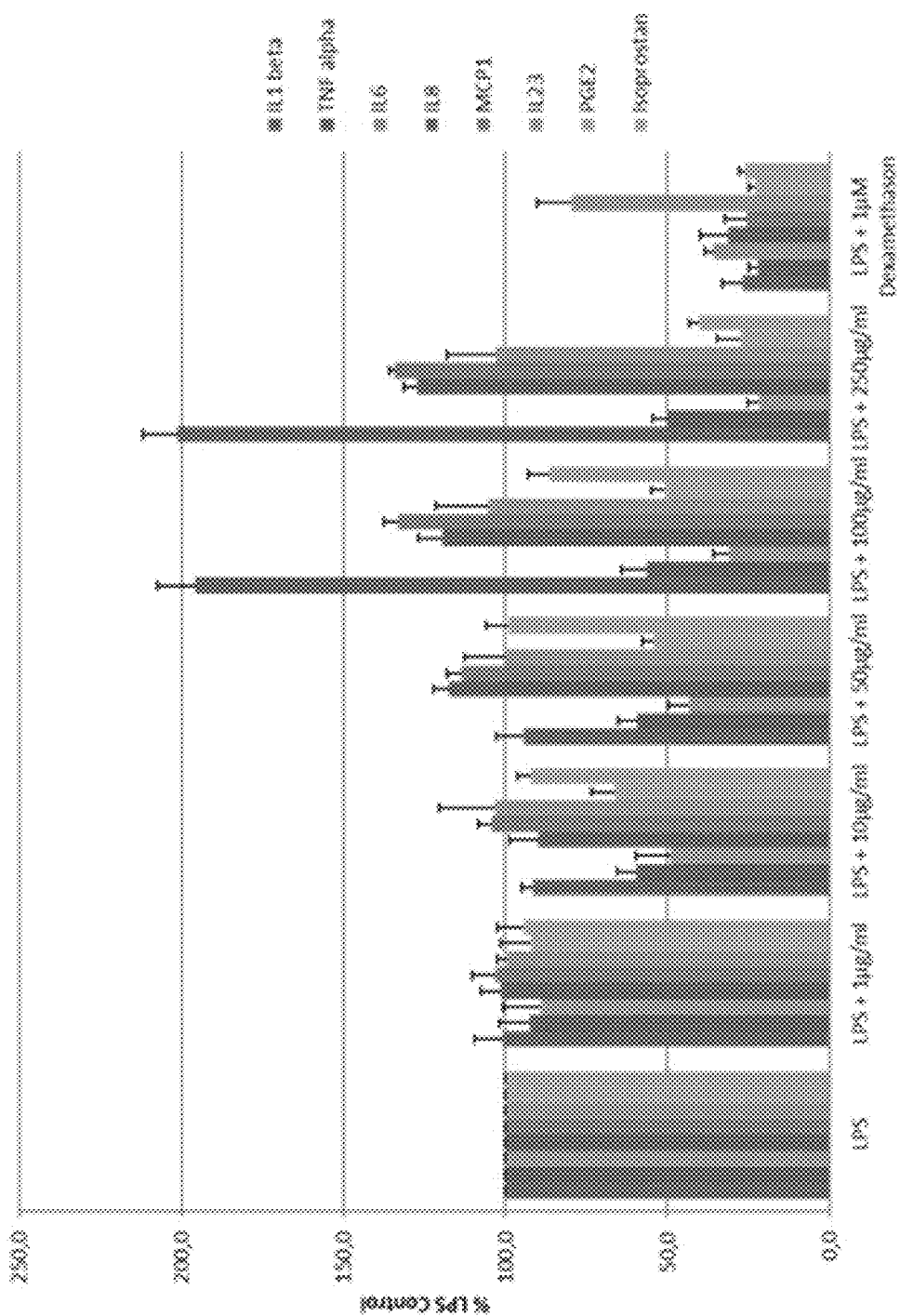
FIG. 1 is a graph depicting exemplary results for the effects of a representative composition on various cytokines in primary human monocytes.

The inventor has now discovered that specific combinations of polyphenol-containing materials (and polyphenols found therein) strongly modulated numerous biomarkers associated with increased or chronic inflammation, NFκB signaling, decreased energy metabolism, senescence, age-related decline in immunity, and/or obesity. Notably, such combinations closely tracked the ingredients and polyphenol-containing materials (and polyphenols found therein) found in the Mediterranean diet. In view of these findings, the inventor therefore contemplates various compositions for nutritional supplements and other nutritional products, compositions, and uses in medicinal food, and even use in medicine.

Based on his extensive research, and as is shown in more detail below, the inventor has now discovered that specific blends of selected plant materials common in the Mediterranean diet (and polyphenols contained therein) can be prepared that mimic the benefits of the Mediterranean diet as evidenced in the modulation of various biomarkers associated with inflammaging and cellular energy. Among other biomarkers, particularly contemplated biomarkers include various pro-inflammatory cytokines and transcription factors (e.g., TNF-alpha, IL-6, $PGE_2$, isoprostane, NFκB), various adipokines (e.g., leptin, oncostatin M, resistin, FGF21, HGF, and IL-11), mitochondrial biogenesis, cellular glucose uptake, intracellular ATP, antioxidant capacity as measured by reactive oxygen species, and expression of various senescence-associated genes.

Notably, the investor discovered that the compositions according to the inventive subject matter will not only inhibit or reduce production and secretion of pro-inflammatory cytokines that operate in distinct inflammation pathways, but also downregulate transcription factors essential to a pro-inflammatory response. Even more unexpected, such modulation of inflammatory components was particularly significant and synergistically enhanced where multiple chemically distinct polyphenol-containing plant materials having a red color, a green color, an orange-yellow color, and a purple-blue color were combined. In still further surprising results, the inventor discovered that the combination of chemically distinct polyphenol-containing plant materials had additional beneficial effects extending well beyond anti-inflammatory effects. Among other things, and as also shown in more detail below, the compositions presented herein had remarkable activity on increasing glucose uptake into a cell and mitochondrial biogenesis, on increasing ATP levels while providing significant antioxidant effect. Moreover, the compositions also exhibited significant impact on selected adipokinins associated with inflammation and energy metabolism. Finally, such compositions also reduced gene expression of various senescence associated genes. These effects, and particularly in aggregate, seem to suggest the same or similar beneficial molecular mechanisms as is typically observed with the Mediterranean diet. Therefore, and without wishing to be bound by a particular theory or hypothesis, the inventor contemplates that the compositions presented herein represent the underlying symphony of biochemically diverse molecules that form the foundation for numerous benefits observed with the Mediterranean diet. In this context, it should also be appreciated that various other diets associated with longevity and healthy ageing (blue zone diets) could be used as a source for ingredients in which polyphenols are present that in concert will enhance pathways and signaling critical for health and lifespan.

Preferably, contemplated blends are combinations of colored plant materials that belong to a number (e.g., at least two, at least three, or at least four) of different color groups, and particularly plant materials having a red color, green color, orange/yellow color, and/or purple/blue color. For example, in one embodiment of such compositions and as shown in more detail below, polyphenol containing products/extracts were obtained from red colored source materials that included an apple extract, a pomegranate extract, tomato powder, and beet root; from green colored source materials that included an olive extract, rosemary extract, green coffee bean extract, and kale; from orange/yellow colored source materials that included an onion extract, a ginger extract, a grapefruit extract, and carrot; and from purple/blue colored source materials that included a grape extract, a blueberry extract, currant, and elderberry, and the particular ingredients and proportions are described in more detail below. Viewed from a different perspective, contemplated compositions will therefore include a large number of polyphenols that below to at least two, or at least three, or at least four different polyphenolic classes, including organic acids, phenolics, flavonols, flavanols, anthocyanins, chlorogenic acids, betacyanins, etc. As will be readily appreciated, the particular choice of a plant material will depend on the desired (polyphenolic) component in the plant material and its effect on a particular biological system and/or signaling pathway.

Of course, it should also be appreciated that the plant materials may be provided in various forms, including whole plant materials or portions thereof (e.g., root, fruit, leaves, etc.) in fresh or dried form, juices or macerates from plant materials or portions thereof in fresh or dried form, and aqueous or aqueous/alcoholic extracts and chromatographic fractions of the aforementioned plant materials. Still further, it should be noted that one or more polyphenols of the plant materials may even be provided as purified (natural isolated or synthetic) chemical entities, typically with a chemical purity of at least 90%, or at least 95%, or at least 98%, or at least 99%. However, it should be recognized that in most embodiments the plant materials will be complex mixtures to provide a combination of desired biological effects on a number of distinct molecular entities (e.g., enzymes, receptors, ion channels) where at least some of the biological effects (e.g., at least one, or at least two, or at least three, etc.) are synergistic. Moreover, it is contemplated that the biological effects on the particular molecular entities will also be complementary and in some instances even synergistic in biological function. Therefore, and based on the testing and desired targets as described in more detail below, it should be appreciated that the compositions of the inventive subject matter may be formulated to meet a particular need. However, in especially preferred aspects contemplated compositions will inhibit multiple targets (e.g., at least two, at least three, at least four, etc.) in multiple and distinct (e.g., at least two, at least three, at least four, etc.) signaling pathways, preferably associated with inflammation, immune response, and/or energy metabolism.

Consequently, and viewed from a different perspective, it should be appreciated that the mechanism of action of contemplated compositions is not limited to a single specific function (e.g., antioxidant) or limited to a specific chemical category (e.g., vitamins), but in fact complementarily and potentially synergistically provides multiple biological activities across distinct metabolic and signaling pathways as well as other significant cellular health functions such as mitochondrial biogenesis and glucose update. As such, contemplated compositions and methods target a variety of biological systems, including energy metabolism, immune function, inflammation, etc. Viewed from a different perspective, contemplated compositions and methods will reduce inflammaging in a subject ingesting such compositions. As used herein, the term "inflammaging" refers to a complex constellation of physiological events that include at least one inflammatory component (e.g., inflammatory condition, overexpression of a pro-inflammatory cytokine, and/or over-activity of a proinflammatory signaling pathways) and at least one typically age-related decline in cellular energy or mitochondrial biogenesis, and/or a continued or increased expression of a senescence-related gene. In addition, it is contemplated that the plant materials will also provide a variety of micro-nutrients to assist or complement the functions of the polyphenols and other colored pigments present in the compositions.

Among other benefits, it should be appreciated that the compositions and methods presented herein will provide notable complementary activity across multiple pathways that control pro-inflammatory signaling and as such will have a more desirable spectrum of physiological effects. For example, and as is shown in more detail below, contemplated compositions not only exhibited significant reduction of pro-inflammatory cytokine release, but also led to a reduction of NFκB signaling, $PGE_2$, adipokine, and isoprostane release, which are further pro-inflammatory mediators operating in separate signaling pathways. Remarkably, while sub-blends of contemplated compositions did show some effect in modulating the above pro-inflammatory mediators, a combination of the sub-blends showed strong synergistic effect in all of the above elements. In addition, the compositions contemplated herein further exhibited a significant antioxidant effect as determined by reduction of reactive oxidative species (ROS), which potentially further reduces cellular stress and pro-inflammatory signaling.

Equally remarkable, contemplated compositions also had significant impact on cellular energy management and particularly on glucose uptake, mitochondrial biogenesis, and ATP levels as is also shown in more detail below. Indeed, contemplated compositions led to unproved glucose uptake that was equivalent to and in some cases even in excess of the effect observed with rosiglitazone, a common anti-diabetic drug. Beneficially, such increased energy uptake did not lead to increased free radical production, but contemplated compositions also significantly stimulated mitochondrial biogenesis and increased intracellular ATP levels. As such, these processes in combination can be viewed as counteracting the age-related decline in energy metabolism. Still further, and with respect to age-related decline, the inventor also discovered that contemplated compositions reduced the expression of numerous senescence-associated genes.

Consequently, it should be appreciated that the compositions contemplated herein may be advantageously used as a stand-alone product to support various aspects of health and healthy ageing such as support of proper immune function, support to reduce inflammation, and support glucose levels (and especially glucose uptake into a cell). Viewed from a different perspective, it should be appreciated that contemplated compositions may be used to treat or reduce a symptom associated with an inflammatory condition, a metabolic dysregulation, a neurological condition, a cardiovascular condition, senescence, and/or oxidative stress. In this context, it should be noted that the term "support" when used in conjunction with a physiological function of condition is intended to mean prevent decline of one or more components or activities of the component(s) associated with the physiological function or condition, at least partially reverse decline of one or more components or activities of the component(s) associated with the physiological function or condition, maintain normal function of one or more components or activities of the component(s) associated with the physiological function condition, prevent abnormal overactivity (or over-expression) of one or more components associated with the physiological function or condition, and/or at least partially reverse abnormal overactivity (or over-expression) of one or more components associated with the physiological function or condition. Alternatively, the compositions contemplated herein may also be combined with other nutritional supplements and/or vitamins to provide beneficial effects otherwise not obtainable with such supplements or vitamins.

With respect to underlying molecular mechanisms for the variety of observed effects using contemplated compositions, the inventor investigated various potential targets that could be positively modulated by contemplated compounds, including various cytokines, NF-κB, various adipokines, glucose uptake, mitochondrial biogenesis, ATP levels, reactive oxygen species, expression of senescence-associated genes, and acetylcholine esterase.

Interleukin-6: Interleukin-6 (IL-6) is a multi-functional cytokine that regulates immune responses, acute phase reactions, and hematopoiesis and may also play a central role in host defense mechanisms. IL-6 is a pleiotropic cytokine produced by a variety of cells. It acts on a wide range of tissues, exerting growth-induction, growth-inhibition, and differentiation respectively, depending on the nature of the target cells. Notably, IL-6 is not produced constitutively by normal cells, but its expression is readily induced by a variety of cytokines, bacterial components such as lipopolysaccharide, or viral infections. IL-6 is typically produced at the site of inflammation, and IL-6 in combination with its soluble receptor sIL-6Rα, dictates the transition from acute to chronic inflammation by changing the nature of leucocyte infiltrate (from polymorphonuclear neutrophils to monocyte/macrophages). In addition, IL-6 exerts stimulatory effects on T- and B-cells, thus favoring chronic inflammatory responses. As such, attempts to downregulate IL-6 and IL-6 signaling are thought to be useful for treatment of various chronic inflammatory diseases (e.g., rheumatoid arthritis). As is shown in more detail below, contemplated compositions had a remarkable impact on IL-6 release and as such are likely contributors to reduction or prevention of one or more symptoms commonly found in (chronic and/or sub-acute) inflammatory disease.

Tumor necrosis factor alpha (TNF-alpha): Tumor necrosis factor-alpha (TNF-alpha) is mainly produced by activated macrophages, T lymphocytes and natural killer (NK) cells and is a central regulator of inflammation, and TNF-alpha antagonists and inhibitors are interesting approaches in treating inflammatory disorders in which TNF-alpha plays an important pathogenetic role. Inhibition of TNF has proven to be an effective therapy for patients with rheumatoid arthritis and other foams of inflammatory disease including psoriasis, psoriatic arthritis, and ankylosing spondylitis, inflammatory bowel disease. Additionally, the efficacy of preventing septic shock and AIDS has also be suggested. Current successful biological therapies include compounds such as etanercept, infliximab, and a fully human monoclonal antibody, adalimumab. However, due to the higher costs and side effects with currently known synthetic antibody therapies, natural TNF inhibitors such as the compositions presented herein present an attractive avenue. Indeed, and as shown in more detail below, contemplated compositions had substantial inhibitory effect on TNF-alpha secretion and as such is also a likely contributor to reduction or prevention of one or more symptoms commonly found in various (chrome and/or sub-acute) inflammatory diseases.

Prostaglandin $E_2$ ($PGE_2$): Prostaglandins (PGs) are the major lipid mediators in animals and are synthesized in vivo from arachidonic acid by the cyclooxygenases (COX-1 or COX-2) as the rate-limiting enzymes. Prostaglandin $E_2$ ($PGE_2$), which is the most abundantly detected PG in various tissues, exerts versatile physiological and pathological actions via four receptor subtypes (EP1-4). Non-steroidal anti-inflammatory drugs, such as aspirin and indomethacin, exert potent anti-inflammatory actions by the inhibition of COX activity and the resulting suppression of PG. $PGE_2$ regulates acute and chronic inflammation, as well as autoimmune diseases at the molecular and cellular levels. One major role of $PGE_2$ in acute inflammation, fever, and pain was understood to be vasodilation of vascular smooth muscle cells. Additional data subsequently demonstrated that $PGE_2$ induces mast cell activation and consequently enhances vascular permeability, contributing to $PGE_2$-induced acute inflammation. Furthermore, $PGE_2$ promotes Th1-cell differentiation, Th17-cell proliferation, and IL-22 production from Th22 cells, and exacerbates chronic inflammation and various autoimmune diseases. Still further, $PGE_2$ induces acute inflammation through mast cell activation via the EP3 receptor. $PGE_2$ also induces chronic inflammation and various autoimmune diseases through T helper 1 (Th1)-cell differentiation. Th17-cell proliferation and IL-22 production from Th22 cells via the EP2 and EP4 receptors. Notably, and as shown in more detail below, the inventor has discovered that the compositions presented herein had a significant inhibitory effect on $PGE_2$ synthesis and release. Therefore, contemplated compositions will once more be a likely contributor to reduction or prevention of one or more symptoms commonly found in various (chrome and/or sub-acute) inflammatory diseases and autoimmune diseases, as well as down-regulators of exacerbated immune responses.

Isoprostanes: Isoprostanes are COX-2 independent mediators of pro-inflammatory accesses and augment perception of pain. Isoprostanes may further contribute to inflammation by increasing neutrophil adhesion to human venous endothelial cells and by increasing endothelial cell permeability in response to oxidative stress. Consequently, contemplated compositions will yet again be a likely contributor to reduction or prevention of one or more symptoms commonly found in various (chronic and/or sub-acute) inflammatory diseases, and particularly those associated with oxidative stress.

Therefore, it should be appreciated that the compositions presented herein had unexpected pleiotropic effects across multiple and distinct pro-inflammatory signaling elements and signaling pathways, potentially leading to broad and systemic reduction of various (chrome and/or sub-acute) inflammatory conditions. Even more unexpectedly, the inventor discovered that the inhibition of IL-6, TNF-alpha, and $PGE_2$ was based on a synergistic effect of various sub-blends present in the compositions presented herein (see data below), and that the inhibitory effect of the sub-blends alone was substantially less pronounced.

In addition to the effect on individual cytokines as noted above, the inventor also discovered that the compositions presented herein had a significant downregulating effect on NF-κB. In this context, it should be appreciated that NF-κB induces the expression of various pro-inflammatory genes, including those encoding cytokines, chemokines, and COX-2, and also participates in inflammasome regulation. In addition, NF-κB plays a critical role in regulating the survival, activation, and differentiation of innate immune cells and inflammatory T cells and as such has effects on innate and target specific immune responses.

NF-κB is highly activated at sites of inflammation in diverse diseases and can also induce transcription of adhesion molecules, MMPs, and inducible nitric oxide (iNOS). For example, in rheumatoid arthritis NF-κB is overexpressed in the inflamed synovium, where its activity may enhance recruitment of inflammatory cells and production of proinflammatory mediators like IL-1, IL-6, IL-8, and TNF-α. Both p50 and p65 have been localized to nuclei in synovial lining cells as well as mononuclear cells in the sub-lining regions. Helicobacter pylori-associated gastritis is also marked by increased NF-κB activity in gastric epithelial cells, and the member of NF-κB positive cells correlates with the degree of gastritis. Similarly, there is evidence of NF-κB activation in inflammatory bowel disease, where lamina propria macrophages display activated p50, c-Rel, and especially p65. Neurological disease and inflammation associated with atherosclerosis are also mediated, in part, by NF-κB. Moreover, inflammatory airway disease in humans has also been associated with cytokine and adhesion molecule expression. This correlates with activation of NF-κB in bronchial biopsies from asthma patients. Increased NF-κB activity with nuclear localization was observed especially in airway epithelial cells, where there is abundant expression of proinflammatory cytokines, chemokines, iNOS, and Cox-2. Other NF-κB associated diseases include atherosclerosis, multiple sclerosis, asthma, inflammatory bowel disease, and systemic inflammatory response syndrome, etc. Therefore, compositions that can modulate NF-κB expression may have significant potential in addressing at least some of the symptoms associated with the inflammatory conditions noted above. Consequently, contemplated compositions will once more be a likely contributor to seduction or prevention of one or more symptoms commonly found in various (chronic and/or sub-acute) inflammatory diseases.

Moreover, and particularly where individuals have an increased body mass index (BMI) or are otherwise overweight or obese, contemplated compositions may have a positive effect on adipokine signaling as discussed and shown in more detail below.

The worldwide epidemic of obesity has brought considerable attention to research aimed at understanding the biology of adipocytes and the events occurring in adipose tissue and in the bodies of obese individuals. Interestingly, accumulating evidence indicates that obesity may cause chronic low-grade (sub-acute) inflammation, which may contribute to systemic metabolic dysfunction that is associated with obesity-linked disorders. Indeed, adipose tissue functions as a key endocrine organ by releasing multiple bioactive substances, known as adipose-derived secreted factors or adipokines, that have in some instances pro-inflammatory or anti-inflammatory activities. Dysregulated production or secretion of these adipokines owing to adipose tissue dysfunction can contribute to the pathogenesis of obesity-linked complications.

Pro-inflammatory adipokines: The production of most adipokines is upregulated in the obese state, and these pro-inflammatory proteins typically function to promote obesity-linked metabolic diseases. In addition to leptin, TNF-alpha, and IL-6, more recently identified adipokines that promote inflammation include resistor, retinol-binding protein 4 (RbP4), lipocalin 2, IL-18, angiopoietin-like protein 2 (ANGPTL2), CC-chemokine ligand 2 (CCL2), CXC-chemokine ligand 5 (CXCL5) and nicotinamide phosphoribosyltransferase (NAMPT). It is the upregulation of these factors (as well as others) that leads to the development of a chronic inflammatory state and contributes to metabolic dysfunction.

Anti-inflammatory adipokines: In addition to the numerous pro-inflammatory adipokines described above, adipose tissues also secrete a smaller number of anti-inflammatory factors, such as adiponectin, which has been the subject of intense investigation, and sFRP5, which has been recently identified as an adipokine.

The inventor has now discovered with regard to adipokine secretion that the compositions presented herein fully inhibited the secretion of IGFBP-1, Leptin, Oncostatin M, and resistin in TNF-alpha induced adipocytes, and the significance of these adipokines is addressed below.

Leptin: The adipokine leptin is the product of the obese gene (ob; also known as Lep), which was identified in ob/ob mice by positional cloning. Leptin regulates feeding behavior through the central nervous system. Mice that lack leptin (ob/ob mice) show hyperphagia (abnormally increased feeding), obesity and insulin resistance, and the administration of leptin to ob/ob mice reverses these changes. The administration of leptin to lipoatrophic mice (which lack subcutaneous adipose tissue and thus have low levels of leptin) also improves metabolic abnormalities, including insulin resistance and hyperlipidermia. Leptin has also been shown to be effective at improving metabolic dysfunction in patients with lipodystrophy or congenital leptin deficiency. However, leptin levels in the blood positively correlate with adipose mass, indicating the occurrence of leptin resistance, and obese individuals have high levels of leptin without the expected anorexic responses. Leptin is structurally similar to the family of helical cytokines that includes IL-2 and growth hormone 1 and is thought to have pro-inflammatory activities. Indeed, leptin increases the production of TNF and IL-6 by monocytes and stimulates the production of CC-chemokine ligands (namely, CCL3, CCL4 and CCL5) by macrophages by activating the JAK2 (Janus kinase 2)-sTAT3 (signal transducer and activator of transcription 3) pathway. In monocytes, leptin also stimulates the production of ROs and promotes cell proliferation and migratory responses. Leptin levels in the serum and adipose tissues are increased in response to pro-inflammatory stimuli, including TNF and lipopolysaccharide (LPs). Furthermore, leptin increases the production of the TH1-type cytokines IL-2 and IFNγ and suppresses the production of the TH2-type cytokine IL-4 by T cells or mononuclear cells thus polarizing T cells towards a TH1 cell phenotype. Consistent with these findings, leptin deficiency protects against liver damage in models of T cell-mediated hepatitis. Thus, it is generally accepted that leptin acts as a pro-inflammatory adipokine.

Oncostatin M (OSM): OSM is a gp130 cytokine with its own specific receptor, OSMR, that heterodimerizes with gp130 and mediates the majority of OSM actions. OSM shares substantial sequence identity with leukemia inhibitory factor (LIF) and can modulate a variety of biological processes, such as liver development and regeneration hepatic insulin resistance and steatosis, inflammation, and cardiomyocyte dedifferentiation and remodeling. Moreover, OSM contributes to the inflammatory state during obesity and may be involved in the development of insulin resistance.

Resistin: Resistin is a member of the cysteine-rich family of resistin-like molecules (RELms) that are associated with the activation of inflammatory processes. Resistin has been shown to induce insulin resistance in mice, and mice lacking resistin have low blood glucose levels post-fasting owing to low hepatic glucose production. Resistin deficiency in ob/ob mice leads to increased obesity, but these severely obese mice have improved glucose tolerance and insulin sensitivity. The ability of resistin to modulate glucose metabolism is associated with the activation of suppressor of cytokine signaling 3 (sOCs3), an inhibitor of insulin signaling, in adipocytes. Although studies in animal models consistently show that resistin promotes insulin resistance, evidence for this effect in humans is less clear. Resistin is present in two quaternary forms: an abundant high-molecular weight hexamer and a less abundant, but more bioactive, trimer, which strongly induces hepatic insulin resistance. In human mononuclear cells, transcription of the resistin gene (RETN) is induced by pro-inflammatory cytokines, including IL-1, IL-6 and TNF, and in white adipose tissue it is inhibited by the PPARγ agonist rosiglitazone, suggesting that the anti-inflammatory effect of rosiglitazone is mediated in part by the attenuation of RETN transcription. More recently, studies of mice that lack endogenous resistin expression in adipocytes but express a human RETN transgene in macrophages indicate that the pro-inflammatory properties of macrophage-derived resistin contribute to insulin resistance in vivo. The pro-inflammatory properties of resistin in human mononuclear cells are evident, as resistin promotes the expression of TNF and IL-6 by these cells. In addition, resistin directly counters the anti-inflammatory effects of adiponectin on vascular endothelial cells by promoting the expression of the pro-inflammatory adhesion molecules vascular cell adhesion molecule 1 (vCAm1) intercellular adhesion molecule 1 (ICAm1) and pentraxin 3 in these cells, thereby enhancing leukocyte adhesion.

IGFBP-1: Insulin-like growth factor-binding protein 1 (IBP-1) also known as placental protein 12 (PP12) is a protein that in humans is encoded by the IGFBP1 gene. The protein binds both insulin-like growth factors (IGFs) I and II and circulates in the plasma. Binding of this protein prolongs the half-life of the IGFs and alters their interaction with cell surface receptors. The IGF system is increasingly implicated in the development of cardiovascular disease. The effects of circulating IGFs on the vasculature are largely modulated by IGFBPs, which control their access to cell-surface IGF receptors. IGFBP-1 has been proposed as the acute regulator of IGF bioavailability because of its metabolic regulation by glucoregulatory hormones. Posttranslational phosphorylation of IGFBP-1 significantly increases its affinity for IGF-1 and therefore represents a further mechanism for controlling IGF bioavailability.

In addition, the inventor has also discovered with regard to adipokine secretion that the compositions presented herein stimulated the secretion of ANGPT-L3, C-Reactive Protein, Endocan, FGF-21, HGF, IGFBP-2, IL-11, RBP4 and Pentraxin 2 in TNF-alpha induced adipocytes (with no observable stimulation in adipocytes induced only with TNF-alpha), and the significance of these induced adipokines is addressed below.

RBP4: Serum RbP4 is a hepatocyte-secreted factor that is responsible for the transport of retinol (vitamin A) throughout the body. Recently, RbP4 was also found to be secreted by both adipocytes and macrophages. The expression of RbP4 is inversely related to that of glucose transporter type 4 (GLuT4; also known as sLC2A4), and administration of recombinant RbP4 to normal mice decreases insulin sensitivity. RbP4 is released by adipocytes and inhibits insulin-induced phosphorylation of insulin receptor substrate 1 (IRs1) in an autocrine or paracrine manner. These data implicate RbP4 as an adipose tissue-secreted factor that is important for the regulation of glucose homeostasis in models of type 2 diabetes.

ANGPTL3: Angiopoietin like protein 3 (ANGPTL3) is best known for its function as an inhibitor of lipoprotein and endothelial lipases. Due to the capacity of genetic or pharmacologic ANGPTL3 suppression to markedly reduce circulating lipoproteins, and the documented cardioprotection upon such suppression, ANGPTL3 has become an emerging therapy target for which both antibody and antisense oligonucleotide (ASO) therapeutics are being clinically tested. While the antibody is relatively selective for circulating ANGPTL3, the ASO also depleted the intra-hepatocellular protein, and there is emerging evidence for cell-autonomous functions of ANGPTL3 in the liver. These include regulation of hepatocyte glucose and fatty acid uptake, insulin sensitivity, LDL/VLDL remnant uptake, VLDL assembly/secretion, polyunsaturated fatty acid (PUFA) and PUFA-derived lipid mediator content, and gene expression.

Fibroblast growth factor 21: Fibroblast growth factor 21 (FGF21) is a protein that in mammals is encoded by the FGF21 gene. The protein encoded by this gene is a member of the fibroblast growth factor (FGF) family and specifically a member of the endocrine subfamily which includes FGF23 and FGF15/19. FGF21 is the primary endogenous agonist of the FGF21 receptor which is composed of the co-receptors FGF receptor 1 and β-Klotho. FGF21 is a hepatokine—i.e., a hormone secreted by the liver—that regulates simple sugar intake and preferences for sweet foods via signaling through FGF21 receptors in the paraventricular nucleus of the hypothalamus and correlates with reduced dopamine neurotransmission within the nucleus accumbens. FGF21 stimulates glucose uptake in adipocytes but not in other cell types. This effect is additive to the activity of insulin. FGF21 treatment of adipocytes is associated with phosphorylation of FRS2, a protein linking FGF receptors to the Ras/MAP kinase pathway. FGF21 injection in ob/ob mice results in an increase in Glut1 in adipose tissue. FGF21 also protects mice from diet-induced obesity when overexpressed in transgenic mice and lowers blood glucose and triglyceride levels when administered to diabetic rodents. Treatment of mice with FGF21 results in increased energy expenditure, fat utilization and lipid excretion.

Interleukin 11: Interleukin 11 (IL-11) is an anti-inflammatory cytokine with receptors located on most cell types and tissues throughout the body. Its anti-inflammatory properties are mediated through suppression of cytokine synthesis, in large part by prevention of NF-kappaB activation. As adipose tissue synthesizes and secretes cytokines involved in establishing insulin resistance and due to the ability of IL-11 to suppress cytokine synthesis, we initiated an investigation to determine the signal transduction pathways initiated by IL-11 in adipose tissue.

Hepatocyte growth factor (HGF): Obesity and its associated chronic inflammation in adipose tissue initiate insulin resistance, which is related to several pathologies including hypertension and atherosclerosis. While body weight in wild-type mice fed with high fat diet (HFD) for 14 weeks was significantly increased accompanied with insulin resistance, HGF-Transgenic mice prevented body weight gain and insulin resistance. The accumulation of macrophages and elevated levels of inflammatory mediators in adipose tissue were significantly inhibited in HGF-Transgenic mice as compared to wild-type mice. The HFD-induced obesity in wild-type mice treated with HGF-neutralizing antibody showed an exacerbated response to the glucose tolerance test. These gain-of-function and loss-of-function studies demonstrated that the elevated HGF level induced by HFD have protective role against obesity and insulin resistance.

IGFBP-2: Proliferation of adipocyte precursors and their differentiation into mature adipocytes contributes to the development of obesity in mammals. IGF-I is a potent mitogen and important stimulus for adipocyte differentiation. The biological actions of IGFs are closely regulated by a family of IGF-binding proteins (IGFBPs), which exert predominantly inhibitory effects. IGFBP-2 is the principal binding protein secreted by differentiating white preadipocytes, suggesting a potential role in the development of obesity. A study with transgenic mice overexpressing human IGFBP-2 under the control of its native promoter demonstrated that overexpression of IGFBP-2 was associated with reduced susceptibility to obesity and improved insulin sensitivity. Whereas wild-type littermates developed glucose intolerance and increased blood pressure with aging, mice overexpressing IGFBP-2 were protected. Furthermore, when fed a high-fat/high-energy diet, IGFBP-2-overexpressing mice were resistant to the development of obesity and insulin resistance. This lean phenotype was associated with decreased leptin levels, increased glucose sensitivity, and lower blood pressure compared with wild-type animals consuming similar amounts of high-fat diet. These findings suggest an important role for IGFBP-2 in obesity prevention.

Glucose uptake and mitochondrial biogenesis: In older adults, skeletal muscle protein synthesis may be resistant to the anabolic action of insulin. Insulin resistance is also associated with activation of muscle proteolysis pathways, which may further lead to muscle loss. In turn, muscle is the primary site for insulin-dependent glucose uptake and reduced muscle surface area for insulin-mediated glucose uptake may further aggravate peripheral insulin resistance, leading to a vicious cycle. Oral insulin sensitizers have been reported to preserve muscle mass although similar associations for muscle strength have yet to be investigated. Interestingly, skeletal muscle mitochondrial function is reduced in type 2 diabetes and may potentially be improved with peripheral insulin sensitization. On this backdrop, the inventor discovered that the compositions presented herein had a significant beneficial effect on glucose uptake in muscle cells as is described in more detail below. Moreover, the benefits of the compositions presented herein also extended to improvements in mitochondrial function, and especially to increased mitochondrial biogenesis as is also shown in more detail below. As such, it should be recognized that the compositions presented herein will not only reduce, but even reverse age-related decline in glucose uptake into muscle but also increase mitochondrial biogenesis.

Intracellular ATP levels were also tested to determine whether the compositions presented herein could increase energy load in a cell. As is shown in more detail below, the level of intracellular ATP was indeed improved, particularly at higher concentration or dosages of contemplate compositions.

Reactive oxygen species: Reactive oxygen species (ROS) typically include derivatives of molecular oxygen that occur as a normal byproducts of aerobic metabolism, and elevated formation of the different ROS generally leads to molecular damage ('oxidative stress'). The ROS, hydrogen peroxide ($H_2O_2$) and the superoxide anion radical ($O_2$—), can act as redox signaling agents at physiological levels and are often generated under the control of growth factors and cytokines by more than 40 enzymes, prominently including NADPH oxidases and the mitochondrial election transport chain, however, prolonged signaling or ROS levels will led to accumulation of oxidative damage and metabolic disturbance. The inventor therefore set out to determine whether contemplated compositions could counteract oxidative stress. Notably, in addition to all beneficial functions as described above, contemplated compositions also exhibited a significant reduction in ROS as is shown in more detail below.

Further, as contemplated compositions were based on components of the Mediterranean diet (which is known to be a common denominator in populations with longevity), the inventor also set out to investigate if the compositions presented herein would have an impact on senescence-associated genes and the exemplary results below demonstrated significant down-regulation of various senescence-associated genes.

Acetylcholinesterase (AChE) is an enzyme found primarily in blood and neural synapses and plays an important role in various cognitive processes. AChE catalyzes the hydrolysis of the neurotransmitter acetylcholine into choline and acetic acid, a reaction necessary to allow a cholinergic neuron to return to its resting state after activation. AChE inhibition (e.g., using donepezil) is an important target for the management of Alzheimer's disease, and AChE inhibitors are the most common drugs used for its management. In addition to Alzheimer's disease, AChE inhibitors have been useful in the diagnosis or treatment of diseases such as glaucoma, myasthenia gravis, and bladder distention. Therefore,, inhibitors of AChE are thought to have pro-cognitive effects. To that end, the inventor also determined if the compositions presented herein would have an inhibitory effect on AChE. Notably, and as demonstrated in more detail below, the compositions presented herein had substantial inhibitory effect on AChE and as such may significantly improve cognition, among other benefits.

In further contemplated aspects of the inventive subject matter, it should be appreciated that the compositions presented herein may be formulated in a variety of forms, and particularly preferred formulations include those in combination with a nutritionally or pharmaceutically acceptable carrier, most preferably for oral administration (however, parenteral administration is also expressly contemplated). Therefore, contemplated compositions can be formulated as solid or a liquid product. For example, where contemplated compositions are formulated as a solid product, suitable product forms include single dosage unit formulations such as capsules, tablets, and powders, while other solid formulations include snack bars, gummies, or other edible products onto which the composition is coated (e.g., onto cereal) or into which the composition is mixed or layered (e.g., into chewing gum). In another examples, where contemplated compositions are formulated as a liquid product, suitable product forms include flavored and/or carbonated beverages (e.g., tea, juice), functional beverages (e.g., sports or energy drinks) or infusions, or liquid dairy product (e.g., yoghourt, kefir).

Therefore, contemplated compositions may be provided in bulk, as part of an edible or drinkable product, and/or provided in single dosage units for consumption. Most typically, the daily dosage for contemplated compositions (excluding the carrier) is preferably at least 10 mg, or at least 50 mg, or at least 100 mg, or at least 200 mg, or at least 300 mg, or at least 400 mg, or at least 500 mg, or at least 750 mg, or at least 1,000 mg, or at least 1,500 mg. For example, suitable dosages will be between 10-50 mg, or between 50-100 mg, or between 100-200 mg, or between 200-400 mg, or between 300-600 mg, or between 400-800 mg, or between 600-1,000 mg, or between 1,000-2,000 mg.

Most typically, contemplated compositions will be orally administered over an extended period of time, such as at least 1 week, or at least 2 weeks, or at least 4 weeks, or at least 2 months, or at least 3 months, or at least 6 months, or at least 1 year and longer to maintain or support healthy ageing. Preferably, administration will be daily, or at least twice a week or at least three times a week. In some embodiments, contemplated compositions may also be topically administered, typically in form of a cream, lotion, essence or elixir, or shampoo. In such case, the compositions may be (optionally filtered) water or hydroalcoholic extracts to so yield a clear solution As will be readily appreciated, contemplated compositions may further be combined with one or more additional ingredients to impart further desirable functionalities, and suitable additional ingredients include vitamins (e.g., single vitamins, or vitamin blends such as multivitamin blends), dietary trace elements or minerals (e.g., individual elements or minerals, or mixtures of multiple elements or minerals in various forms), various specialty compounds and mixtures (e.g., prebiotics, human milk oligosaccharides), and/or one or more probiotic microorganisms (e.g., *Lactobacillus* spec., *Bifidobacterium* spec., *Leukonostoc* spec., *Saccharomyces boulardii*, etc.), postbiotics (e.g., short chain fatty acids such as butyrate, secondary bile acids such as (tauro)ursodeoxycholic acid, etc.), dietary fiber (e.g., soluble fibers or insoluble fibers), and/or nutritionally acceptable oligosaccharides (e.g., Xylo-oligo-saccharides (XOS) or fructo-oligo-saccharides (FOS)). Similarly, contemplated compositions may also include niacin, niacinamide, nicotinamide riboside, nicotinamide mononucleotide, nicotinamide adenine dinucleotide, and/or a nutritionally acceptable CD38 inhibitor to thereby increase intracellular NAD and/or NADP levels (and their respective reduced forms NADH and NADPH). As such, contemplated compositions may particularly further (synergistically) enhance or support cellular metabolism and energy.

Of course, it should be recognized that the compositions according to the inventive subject matter may be administered not only to a human, but also to other non-human mammals, and especially livestock and companion animals (e.g., dogs, cats, horses). Administration will typically be between once daily and three times daily (and in some cases even more) over a period of at least two days, three days, five days, 1 week, 2-4 weeks, 1-3 months, and even longer. Most typically, administration can be performed for a period sufficient to provide at least symptomatic relief of a condition (e.g., pain and swelling associated with inflammation, low energy level, frequent infections, etc.), or prophylactially to avoid or help reduce severity of a health condition.

EXAMPLES

Representative Composition

Unless indicated otherwise, all tests were performed with a defined mixture of selected polyphenol-containing products/extracts common to the Mediterranean diet. The polyphenol-containing products/extracts were obtained from source materials characterized by color as follows: Red group (sub-blend): apple extract, pomegranate extract, tomato powder, and beet root; Green group (sub-blend): olive extract, rosemary extract, green coffee bean extract, and kale; Orange/yellow group (sub-blend): onion extract, ginger extract, grapefruit extract, and carrot; and Purple/blue group (sub-blend): grape extract, blueberry extract, currant, and elderberry. Corn starch, silica, and sunflower lecithin were used as processing aids. Relative proportions are shown in Table 1 below.

TABLE 1

| Ingredient | Wt % | Part | Solvent | Standardized to | State |
|---|---|---|---|---|---|
| Grape Extract | 15.75 | Whole fruit | Ethanol | Min 50% total Proanthocyanidins | Powdered |
| Apple Extract | 10.00 | Whole fruit | Ethanol/Water | 70% Polyphenols | Powdered |
| Ginger Extract | 10.00 | Root | Ethanol/Water | 5% Gingerol | Powdered |
| Onion Extract | 10.00 | Root bulb | Ethanol/Water | 30% Quercetin | Powdered |
| Pomegranate Extract | 10.00 | Whole fruit | Ethanol | 40% Punicalagins | Powdered |
| Green Coffee Bean Extract | 7.50 | Seed | Ethanol/Water | 50% Chlorogenic Acids | Powdered |
| Rosemary Extract | 7.50 | Leaves | Ethanol/Water | 15% Rosmarinic Acid | Powdered |
| Olive Extract | 6.38 | Whole fruit | Water | 12% Hydroxytyrosol | Powdered |
| Maltodextrin | 3.19 | —/— | —/— | —/— | Powdered |
| Blueberry Extract | 2.50 | Whole fruit | Ethanol/Water | 12% Anthocyanins | Powdered |
| Grapefruit Extract | 2.50 | Whole fruit | Ethanol/Water | 90% Naringin | Powdered |
| Kale | 2.50 | Leaves | None | —/— | Powdered |
| Beet Root | 2.45 | Root | None | —/— | Powdered |
| Carrot | 2.45 | Root | None | —/— | Powdered |
| Black Currant | 2.43 | Whole fruit | None | —/— | Powdered |
| Elderberry | 2.43 | Whole fruit | None | —/— | Powdered |
| Tomato | 1.85 | Whole fruit | None | —/— | Powdered |
| Corn Starch | 0.31 | —/— | —/— | —/— | Powdered |
| Silica | 0.25 | —/— | —/— | —/— | Powdered |
| Sunflower Lecithin | 0.03 | —/— | —/— | —/— | Powdered |

Phytochemical HPLC/MS/MS analysts: An HPLC/MS compositional analysis of the exemplary composition above revealed the following ingredients and proportions where the columns in each of Tables 2-8 indicate the analyte ID (col.1), chemical entity (col.2), M-H (col.3), RT (col.4), peak intensity (col.5). and MS/MS fragments (col.6):

TABLE 2

| | | Organic acids | | | |
|---|---|---|---|---|---|
| 1 | Citric acid | 191.0186 | 2.9 | 5.25E+08 | 102, 111, 129, 173 |
| 2 | Malic acid | 133.0130 | 2.2 | 1.26E+08 | 71, 89, 115 |
| 3 | Glucaric acid | 209.0291 | 1.7 | 8.68E+08 | 133, 147, 191 |
| 4 | Gluconic acid | 195.0504 | 1.7 | 4.44E+08 | 99, 129, 159, 177 |
| 5 | hydroxy jasmonic acid-O-glucoside | 387.1668 | 22.3 | 2.23E+08 | 59, 163, 207 |
| 6 | Azelaic acid | 187.0968 | 28.3 | 1.56E+07 | 125, 169 |
| 5 | Arabinonic acid | 165.0395 | 1.7 | 1.96E+08 | 129, 147, 165 |

TABLE 3

| | | Phenolics | | | |
|---|---|---|---|---|---|
| 7 | Coumaric acid | 163.0389 | 24.3 | 9.19E+06 | 119, 147 |
| 8 | Coumaric aicd - derv | 295.0460 | 21.1 | 2.45E+06 | 119, 163 |
| 9 | Quinic acid-I | 191.0553 | 1.8 | 4.76E+08 | 173 |
| 10 | Quinic acid-II | 191.0553 | 20.1 | 2.40E+08 | 173 |
| 11 | Caffeic acid | 179.0341 | 21.4 | 1.54E+08 | 135 |
| 12 | Caffeic acid-hexose-I | 341.0869 | 16.6 | 5.02E+06 | 135, 161, 179 |
| 13 | Caffeic acid-hexose-II | 341.0869 | 18.5 | 1.28E+07 | 135, 161, 179 |
| 14 | Caffeic acid-hexose-III | 341.0869 | 19.6 | 1.02E+07 | 135, 179 |
| 15 | Caffeic acid-hexose-IV | 341.0869 | 20.0 | 1.61E+07 | 135, 161, 179 |
| 16 | Ferulic acid | 193.0498 | 25.6 | 4.32E+06 | 134.04, 149.06, 178.03 |
| 17 | Ferulic acid-hexose-I | 355.1028 | 21.7 | 1.97E+07 | 175 |
| 18 | Ferulic acid-hexose-I | 355.1028 | 22.5 | 5.63E+06 | |
| 19 | Ferulic acid-hexose-I | 355.1028 | 23.3 | 6.47E+06 | 134, 149, 175 |

TABLE 3-continued

| | Phenolics | | | | |
|---|---|---|---|---|---|
| 20 | Ferulic acid-hexose-I | 355.1028 | 24.9 | 3.24E+06 | 193 |
| 21 | Ferulic acid-hexose-I | 355.1028 | 25.9 | 4.32E+06 | 193 |
| 22 | 3,4-Dihydroxybenzoic acid | 153.0188 | 10.2 | 1.23E+07 | 109 |
| 23 | Gallic acid | 169.0132 | 5.3 | 6.41E+07 | 125 |
| 24 | Rosmaric acid | 359.0772 | 28.8 | 1.18E+09 | 135, 131, 179, 197 |
| 25 | Rosmaric acid dimer | 719.1618 | 28.8 | 5.48E+08 | 135, 161, 179, 197 |
| 26 | Salvianic acid A | 197.0447 | 9.2 | 7.12E+07 | 123, 135, 179, 180 |
| 27 | Ethyl gallate | 197.0449 | 24.3 | 1.83E+07 | 125, 151, 169 |
| 28 | Ellagic acid | 300.9994 | 25.8 | 1.20E+08 | 229, 257, 283 |
| 29 | Ellagic acid glucoside | 463.0529 | 22.9 | 5.69E+05 | 125, 169, 300.99, 463 |
| 30 | Galloyl-HHDP-glucoside (Corilagin) | 633.0737 | 22.7 | 6.10E+07 | 125, 169, 193, 275, 300.99 |
| 31 | Digalloyl-HHDP-glucoside | 785.0867 | 22.3 | 1.92E+06 | 125, 169, 275, 300.99 |
| 32 | 3-Galloylquinic acid (Theogallin) | 343.0673 | 5.9 | 1.70E+06 | 169, 191 |
| 33 | 3,4-Dihydroxybenzoic | 153.0183 | 10.3 | 1.23E+07 | 96, 109 |
| 34 | 3,4-Dihydroxybenzoic | 153.0545 | 10.3 | 3.62E+08 | 109, 123, 153.0182 |
| 35 | 2,4-Dihydroxybenzoic | 153.0183 | 23.8 | 8.71E+06 | 109 |
| 36 | 2-Hydroxybenzoic acid | 137.0232 | 15.0 | 1.10E+07 | 93 |

TABLE 4

| | Flavonoids | | | | |
|---|---|---|---|---|---|
| 37 | Naringenin | 271.0604 | 34.4 | 2.96E+07 | 119, 151, 227, 271 |
| 38 | Naringenin-glucoside | 433.1149 | 28.0 | 4.14E+06 | 151, 271 |
| 39 | Naringenin-rhamnoglucoside | 579.1722 | 27.5 | 1.13E+09 | 151, 271, 549 |
| 40 | Naringenin-rhamnoglucoside dimer | 1159.3540 | 27.5 | 5.66E+07 | 151, 271, 459 |
| 41 | Myricetin | 317.0503 | 29.0 | 1.09E+07 | 137, 151, 178 |
| 42 | Myricetin 3-rhamnoside | 463.0894 | 25.8 | 5.61E+06 | 316, 317 |
| 43 | Myricetin 3-glucoside I | 479.0839 | 24.3 | 4.59E+06 | 316, 317 |
| 44 | Myricetin 3-rhamnoside II | 479.0839 | 24.5 | 4.57E+06 | 316, 317 |
| 45 | Phloretin | 273.0769 | 34.5 | 2.41E+08 | 167 |
| 46 | Phloretin-glucoside | 435.1298 | 29.0 | 2.85E+08 | 167, 273 |
| 47 | Phloretin-arabinose-glucoside | 567.1733 | 27.5 | 3.28E+08 | 167, 273 |
| 48 | Phloretin-diglucoside | 597.1831 | 26.8 | 7.70E+06 | 167, 273 |
| 49 | Apigenin | 269.0460 | 34.4 | 4.46E+07 | 151 |
| 50 | Apigenin glucoside | 431.0985 | 27.8 | 1.36E+07 | 268, 269 |
| 51 | Apigenin rhamnoside glucoside | 577.1575 | 27.4 | 8.96E+07 | 269 |
| 52 | Apigenin rhamnoside glucoside der | 623.1635 | 27.4 | 7.88E+06 | 269, 577 |
| 53 | Apigenin rhamnoside glucoside dimer | 1155.3230 | 27.4 | 1.41E+06 | 269, 577 |
| 54 | Quercetin | 301.0348 | 32.1 | 1.89E+09 | 151, 179, 273, 301 |
| 55 | Quercetin dimer | 603.0795 | 32.1 | 3.94E+08 | 151, 178, 301 |
| 56 | Quercetin galactoside | 463.0874 | 24.6 | 1.00E+07 | 301 |
| 57 | Quercetin glucoside-1 | 463.0874 | 25.9 | 2.98E+07 | 151 |
| 58 | Quercetin glucoside-2 | 463.0874 | 26.1 | 7.16E+07 | 151, 300, 301 |
| 59 | Quercetin-diglucoside | 625.1400 | 23.8 | 8.83E+05 | 151, 178, 301, 463 |
| 60 | Quercetin-rutinoside or Rutin | 609.1478 | 25.5 | 3.37E+07 | 300, 301 |
| 61 | Luteolin | 285.0407 | 31.9 | 4.20E+07 | 133.03, 199.04, 217.05, 241 |
| 62 | Luteolin glucoside 1 | 447.0938 | 26.2 | 4.58E+06 | 284, 285 |
| 63 | Luteolin glucoside 2 | 447.0938 | 24.6 | 1.50E+07 | 284, 285 |
| 64 | Catechin-1 | 289.0704 | 20.2 | 5.97E+08 | 151, 179, 205, 245 |
| 65 | Catechin-2 | 289.0704 | 22.7 | 8.47E+08 | |
| 66 | Proanthocyanidin B1 | 577.1364 | 22.0 | 4.06E+06 | 125, 289, 407 |
| 67 | Proanthocyanidin B2 | 577.1364 | 18.9 | 2.14E+08 | 125, 289, 407 |
| 68 | Isorhamnetin | 315.0503 | 35.4 | 2.66E+08 | 300, 315 |
| 69 | Isorhamnetin glucoside | 477.1030 | 26.7 | 1.11E+08 | 119, 151, 299, 314, 315 |
| 70 | Isorhamnetin diglucoside-1 | 639.1563 | 27.4 | 1.11E+06 | 151, 285, 313, 315, 476, 477, 639 |
| 71 | Isorhamnetin-rhamnosyl-glucoside | 623.1939 | 26.1 | 6.63E+06 | 315 |
| 72 | Kaempferol | 285.0397 | 35.0 | 1.27E+08 | 125.02, 244, 257, 268 |
| 73 | Kaempferol glucoside-1 | 447.0938 | 26.9 | 4.02E+06 | |
| 74 | Kaempferol glucoside-2 | 447.0938 | 27.4 | 1.98E+07 | |
| 75 | Kaempferol glucoside-3 | 447.0938 | 27.6 | 1.04E+07 | |
| 76 | Kaempferol glucoside-4 | 447.0938 | 27.9 | 4.47E+06 | |
| 77 | Kaempferol-3-O-rutinoside | 593.1521 | 25.6 | 1.68E+07 | 285 |
| 78 | Kampferol 3-(6-glucosylglucoside) 7-rhamnoside | 755.2060 | 25.9 | 1.23E+06 | 285 |
| 79 | wogonin | 283.0616 | 41.2 | 1.42E+08 | 268, 283 |

TABLE 5

| | Anthocyanin | | | |
|---|---|---|---|---|
| 80 | Cyanidin-3-O-glucoside | 449.1073 | 21.1 | 1.67E+07 287 |
| 81 | Cyanidin derv | 463.0874 | 27.7 | 3.56E+05 287 |
| 82 | Cyanidin derv | 463.0874 | 29.1 | 1.97E+07 287 |
| 83 | Cyanidin-3-O-rutinoside | 595.1658 | 25.6 | 8.57E+05 287, 449 |
| 84 | Cyanidin 3-sambubioside | 581.1500 | 21.1 | 5.95E+06 287 |
| 85 | Pelargonidin | 271.0600 | 24.5 | 2.10E+06 271 |
| 86 | Pelargonidin-glucoside | 433.1131 | 27.9 | 7.85E+05 271 |
| 87 | Pelargonidin-glucoside derv | 639.1710 | 31.4 | 5.30E+05 175, 207, 271 |
| 88 | Malvidin | 331.0809 | 26.7 | 2.27E+06 316 |

TABLE 5-continued

| | Anthocyanin | | | |
|---|---|---|---|---|
| | arabinoside-I | | | |
| 95 | Petunidin | 317.0655 | 35.5 | 2.77E+06 317 |
| 96 | Petunidin 3-glucoside | 479.1186 | 26.7 | 1.32E+07 317 |
| 97 | Petunidin 3-rutinoside | 625.1765 | 26.1 | 5.63E+05 317 |
| 98 | Petunidin derv | 463.0874 | 26.9 | 4.03E+05 317 |
| 99 | Peonidin | 301.0709 | 34.8 | 1.63E+06 286 |
| 100 | Peonidin-glucoside-I | 463.1240 | 26.9 | 2.77E+06 301 |
| 101 | Peonidin-glucoside II | 463.1240 | 28.3 | 6.98E+06 301 |
| 102 | Peonidin-rutinoside | 609.1814 | 27.6 | 1.52E+06 301 |
| 103 | Peonidin-feruloyl-glucoside | 639.1710 | 31.7 | 1.88E+06 177, 301 |

TABLE 6

| | Chlorogenic acids | | | |
|---|---|---|---|---|
| 104 | 3-Caffeoylquinic acid | 353.0875 | 14.3 | 2.70E+08 135, 179, 191 |
| 105 | 5-Caffeoylquinic acid | 353.0875 | 20.1 | 8.52E+08 179, 191 |
| 106 | 4-Caffeoylquinic acid | 353.0875 | 21.1 | 5.09E+08 135, 173, 179, 191 |
| 107 | 3-Caffeoylquinic acid dimer | 707.1830 | 14.3 | 1.87E+07 135, 179, 191, 353 |
| 108 | 5-Caffeoylquinic acid dimer | 707.1833 | 20.1 | 9.23E+08 191, 353 |
| 109 | 4-Caffeoylquinic acid dimer | 707.1834 | 21.1 | 1.95E+08 135, 173, 179, 191, 353 |
| 110 | 3-Caffeoylshikimic acid | 335.0770 | 24.2 | 3.17E+07 135, 161, 173, 179 |
| 111 | 4-Caffeoylshikimic acid | 335.0770 | 24.5 | 1.62E+08 135, 161 |
| 112 | 5-Caffeoylshikimic acid | 335.0770 | 25.0 | 1.53E+08 161 |
| 113 | 3,4-Dicaffeoylshikimic acid | 497.1091 | 29.5 | 0 |
| 114 | 3,5-Dicaffeoylshikimic acid | 497.1091 | 32.0 | 9.10E+07 161, 179 335 |
| 115 | 4,5-Dicaffeoylshikimic acid | 497.1091 | 32.7 | 6.97E+06 135, 161, 179, 335 |
| 116 | 3-Feruloylquinic acid | 367.1032 | 20.7 | 1.13E+08 134, 193 |
| 117 | 5-Feruloylquinic acid | 367.1032 | 23.6 | 3.76E+08 163, 191 |
| 118 | 4-Feruloylquinic acid | 367.1035 | 23.8 | 1.66E+08 173, 193 |
| 119 | 3-Feruloylquinic acid dimer | 735.2144 | 20.7 | 7.14E+05 |
| 120 | 5-Feruloylquinic acid dimer | 735.2144 | 23.6 | 1.03E+08 173, 191, 367 |
| 121 | 4-Ferloylquinic acid dimer | 735.2144 | 23.8 | 4.17E+06 173, 193, 367 |
| 122 | 3-Coumaroylquinic acid | 337.0932 | 19.0 | 2.68E+07 119, 163 |
| 123 | 4-Coumaroylquinic acid | 337.0933 | 22.6 | 9.95E+07 191 |
| 124 | 5-Coumaroylquinic acid | 337.0933 | 23.0 | 4.09E+08 163, 173 |
| 125 | 3-Coumaroylquinic acid dimer | 675.1941 | 19.0 | 0 |
| 126 | 4-Coumaroylquinic acid dimer | 675.1941 | 22.6 | 3.00E+06 191 |
| 127 | 5-Coumaroylquinic acid dimer | 675.1941 | 23.0 | 1.53E+07 163, 173 |
| 128 | 3,4-Dicaffeoyl quinic acid | 515.1189 | 27.1 | 2.63E+08 135, 161, 173, 179, 191, 353 |
| 129 | 3,5-Dicaffeoyl quinic acid | 515.1190 | 27.6 | 1.79E+08 135, 179, 191, 353 |
| 130 | 4,5-Dicaffeoyl quinic acid | 515.1195 | 28.3 | 3.37E+08 135, 173, 179, 191, 353 |
| 131 | Valeroylquinic acid ssomer-X | 275.1135 | 14.9 | 2.70E+05 101, 173, 181 |
| 132 | Valeroylquinic acid isomes-2 | 275.1135 | 15.8 | 5.75E+05 101, 181, 191 |
| 133 | Valeroylquinic acid isomer-3 | 275.1135 | 21.0 | 1.17E+06 101, 173 |
| 134 | Valeroylquinic acid isomer-4 | 275.1133 | 21.4 | 2.26E+06 101, 173 |
| 135 | Valeroylquinic acid isomer-5 | 275.1135 | 23.2 | 3.27E+05 93, 101, 173, 181, 191 |
| 136 | Valeroylquinic acid isomer-6 | 275.1135 | 23.4 | 5.25E+05 101, 173 |
| 137 | Valeroylquinic acid isomer-7 | 275.1135 | 30.4 | 5.22E+06 93, 101, 173, 181, 191 |
| 138 | Valeroylquinic acid isomer-8 | 275.1135 | 30.6 | 1.18E+06 101 |
| 139 | Valeroylquinic acid isomer-9 | 275.1135 | 31.7 | 1.98E+06 101, 173 |
| 140 | Caffeoylvaleroylquinic acid isomer 1 | 437.1451 | 29.7 | 3.55E+06 161, 173, 179, 275 |
| 141 | Caffeoylvaleroylquinic acid isomer 2 | 437.1451 | 29.8 | 6.88E+06 161, 173, 179, 275 |
| 142 | Caffeoylvaleroylquinic acid isomer 3 | 437.1451 | 30.4 | 2.46E+06 161, 173, 179, 275 |
| 143 | Caffeoylvaleroylquinic acid isomer 4 | 437.1451 | 30.6 | 5.13E+06 173, 275 |
| 144 | Caffeoylvaleroylquinic acid isomer 5 | 437.1451 | 31.7 | 6.96E+06 173, 275 |
| 145 | Quinic acid-glucoside-R*-1 | 481.2442 | 24.8 | 3.81E+07 161, 197, 301 |
| 146 | Quinic acid-glucoside-R*-2 | 481.2442 | 25.3 | 1.22E+08 161, 197, 301 |
| 147 | Valeroylquinic acid glucoside-R*-1 | 565.3023 | 33.3 | 1.18E+07 301, 463, 481 |
| 148 | Valeroylquinic acid diglucoside-R*-1 | 727.3545 | 26.6 | 3.83E+06 161, 301, 323, 481, 643 |
| 149 | Valeroylquinic acid diglucoside-R*-2 | 727.3545 | 30.4 | 1.89E+06 205, 361, 625, 643 |
| 150 | Valeroylquinic acid diglucoside-R*-3 | 727.3545 | 30.8 | 3.05E+07 481, 523, 625, 643 |

TABLE 5-continued

| | Anthocyanin | | | |
|---|---|---|---|---|
| 89 | Malvidin arabinoside | 463.1237 | 23.0 | 8.98E+06 331 |
| 90 | Malvidin-feruloyl-arabinoside | 639.1710 | 28.1 | 7.34E+05 331 |
| 91 | Delphinidin | 303.0496 | 32.2 | 2.73E+07 303 |
| 92 | Delphinidin 3-glucoside | 465.1028 | 20.1 | 6.49E+06 303, 385 |
| 93 | Delphinidin 3-rutinoside | 611.1603 | 25.5 | 1.30E+06 303 |
| 94 | Delphinidin-3- | 435.0922 | 20.7 | 2.06E+06 303 |

TABLE 7

| | Betacyanin | | | |
|---|---|---|---|---|
| 151 | Betanin | 551.1517 | 15.6 | 2.19E+04 |
| 152 | Isobetanin | 551.1517 | 19.7 | 1.54E+04 |

TABLE 8

| Amino acids, alkaloids & other compounds | | | | |
| --- | --- | --- | --- | --- |
| 153 Glycerophosphocholine | 258.1098 | 1.7 | 6.17E+07 | 104 |
| 154 Adenosine | 268.1040 | 4.1 | 4.68E+06 | 136 |
| 155 Phenylalanine | 166.0861 | 6.8 | 1.41E+07 | 120 |
| 156 Tryptophan | 205.0973 | 14.5 | 6.28E+06 | 146, 188 |
| 157 Tyrosine | 182.0812 | 3.7 | 9.16E+06 | 119, 123, 136, 147, 165 |
| 158 Dopamine | 154.0858 | 2.7 | 8.64E+06 | 113, 137 |
| 159 Trigonellin | 138.0548 | 1.8 | 2.05E+08 | 94 |
| 160 Caffeine | 195.0875 | 20.1 | 4.94E+07 | 138 |
| 161 Xanthine | 151.0256 | 3.1 | 7.74E+05 | 109 |

Unless expressly stated otherwise, activity of the representative composition was tested for modulating effects on various target entities that are associated with mild/chronic inflammation, age-related decline of immunity, energy metabolism, senescence, reactive oxygen species, acetylcholine esterase activity, obesity, and viability, and exemplary activity results are presented below.

Cytokines

In the following experiments, the inventor performed a series of tests to determine the effect of the representative composition and sub-blends on various cytokines. To that end, the tested compositions were used with LPS-treated primary human monocytes and with SEB-induced T-lymphocytes (T-helper cells, CD4+) to determine the specific reactions with regard to selected pro-inflammatory cytokines. Unless stated otherwise, all tested materials were provided as solid powders that were dissolved in water.

Here, the inventor used primary human monocytes/lymphocytes to test the anti-inflammatory effects of the test articles as described in more detail below using well established and published methods. Human monocytes are one of the major cell type involved in peripheral inflammation since they are the cells mainly affected by bacterial lipopolysaccharide (LPS) produced by gram-negative bacteria. Moreover, cytokine release from monocytes is also thought to be one of the first steps in the inflammatory cascade, and typical cytokines include interleukin-1 (IL-1) beta, IL-6, IL-8, IL-23, and tumor necrosis factor (TNF) alpha along with other pro-inflammatory cytokines such as prostaglandin E2 ($PGE_2$), certain chemokines such as monocyte chemoattractant protein-1 (MCP-1, also known as CCL2), and macrophage inflammatory protein-1 (MIP-1), and free radicals and oxidative stress markers such as isoprostane. While monocytes also trigger an inflammatory cascade in other cell types such as fibroblasts etc., T cells are responsive to cytokine signaling and play a central role in the adaptive immune response.

T cells can be easily distinguished from other lymphocytes by the presence of a T-cell receptor (TCR) on their cell surface. Interleukin-2 (IL-2) is a 15.5-16 kDa protein primarily produced by activated CD4+ T cells (T helper cells) e.g., by enterotoxin type B, also known as *Staphylococcal* enterotoxin B (SEB), which is an enterotoxin produced by the gram-positive bacteria *Staphylococcus aureus*. IL-2 regulates the activities of white blood cells (leukocytes, often lymphocytes) that are responsible for immunity. IL-2 is part of the body's natural response to microbial infection, and in discriminating between foreign ("non-self") and "self". The parameters investigated are well established inflammatory mediators all known to be involved in inflammation and playing an important role in inflammatory cascade by inducing pain and inflammation.

Measurement of cytokines in primary human monocytes: Human primary monocytes are isolated (enriched) from buffy coats of healthy human blood donors. Cells are seeded in 24-well-plates (approx. 500 000 cells/ml in 1 ml) for ELISA experiments. Cells are incubated with LPS (10 ng/ml) for 24 h. The representative composition (5 doses) and dexamethasone as anti-inflammatory control were added 30 min before LPS treatment (untreated cells served as negative control). After 24 h, supernatants were removed, centrifuged, and investigated for the requested inflammatory parameters such as MCP-1, IL-8, IL-6, IL-23, and TNF-alpha concentrations using ELISAs (MCP-1, TNF-alpha, IL-6, IL-23, and IL-8, R&D/Biotechne) using manufacturer's protocol. Each dose was investigated 6 times in two-three buffy coats from 2-3 different donors (n=2-3 per buffy coat, n=6 in total).

Measurement of PGE2 and isoprostane (free radical marker) in primary human monocytes: Human primary monocytes were isolated (enriched) from buffy coats of healthy human blood donors. Cells were seeded in 24-well-plates (approx. 500 000 cells/ml in 1 ml) for EIA experiments. Cells were incubated with LPS (10 ng/ml) for 24 h. The representative composition (5 doses) and dexamethasone as anti-inflammatory control are added 30 min before LPS treatment (untreated cells serve as negative control). After 24 h, supernatants were removed, centrifuged, and investigated for isoprostane and PGE2 concentrations using EIAs (from Cayman, distributed by Biomol, Hamburg, Germany). Each dose was investigated 6 times in two-three buffy coats from 3 different donors (n=2-3 per buffy coat, n=6 in total).

Measurement of IL-2 in primary T cells: Human primary T-cells are isolated (enriched) from buffy coats of healthy human blood donors. Cells are seeded in 24-well-plates (approx. 500 000 cells/ml in 1 ml) for ELISA experiments. Cells are incubated with SEB (1 µg/ml) for 24 h. The representative composition (5 doses) and dexamethasone or hydrocortisone as anti-inflammatory control were added 30 min before SEB treatment (untreated cells serve as negative control). After 24 hr, supernatants were removed, centrifuged, and investigated for IL-2 concentrations using ELISA (Biotechne, Wiesbaden, Germany) using manufacturer's protocol (other parameters are also possible). Each dose was investigated 6 times in two-three buffy coats from 2-3 different donors (n=2-3 per buffy coat, n=6 in total).

Figure 2:
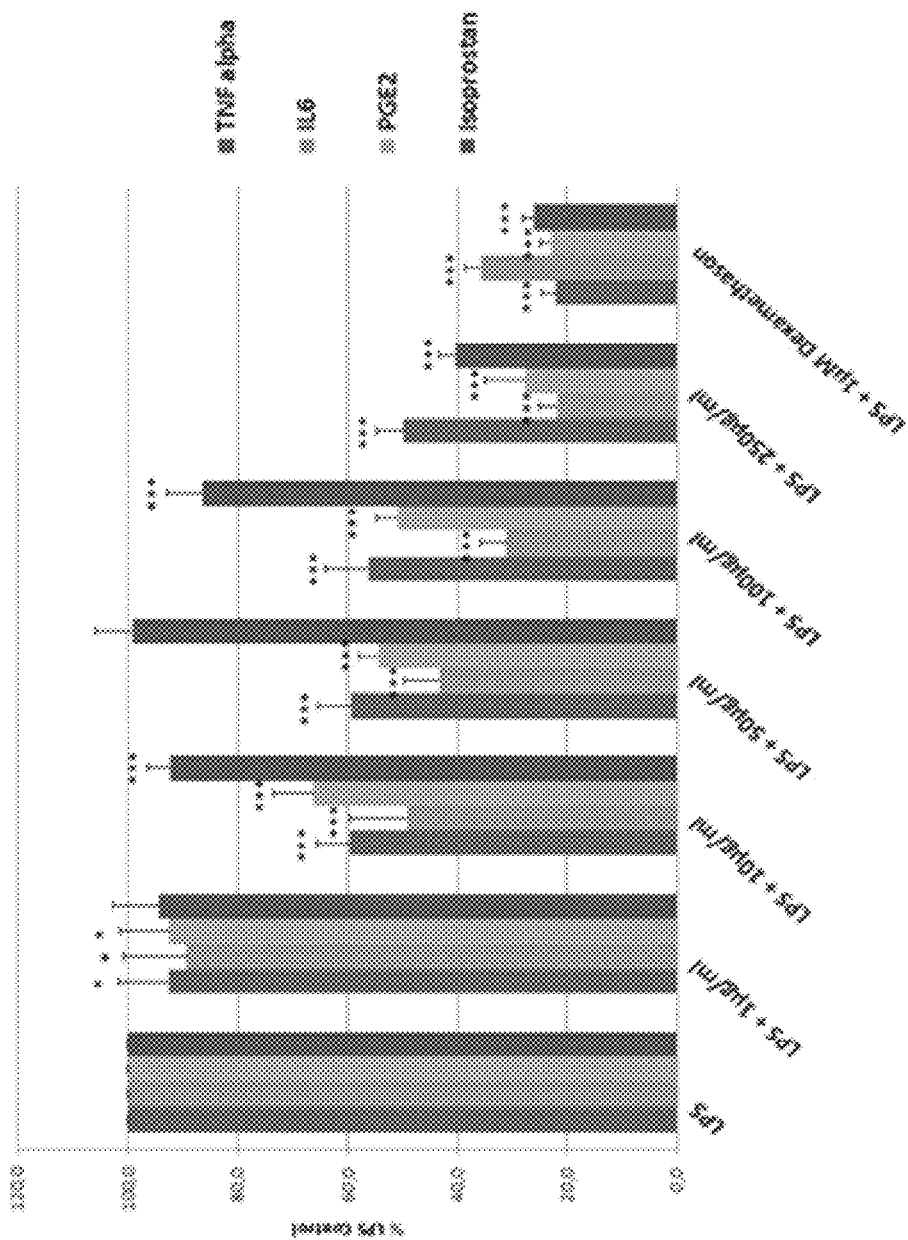
FIG. 2 is a graph depicting exemplary results for the effects of a representative composition on selected cytokines in primary human monocytes.
Figure 3:
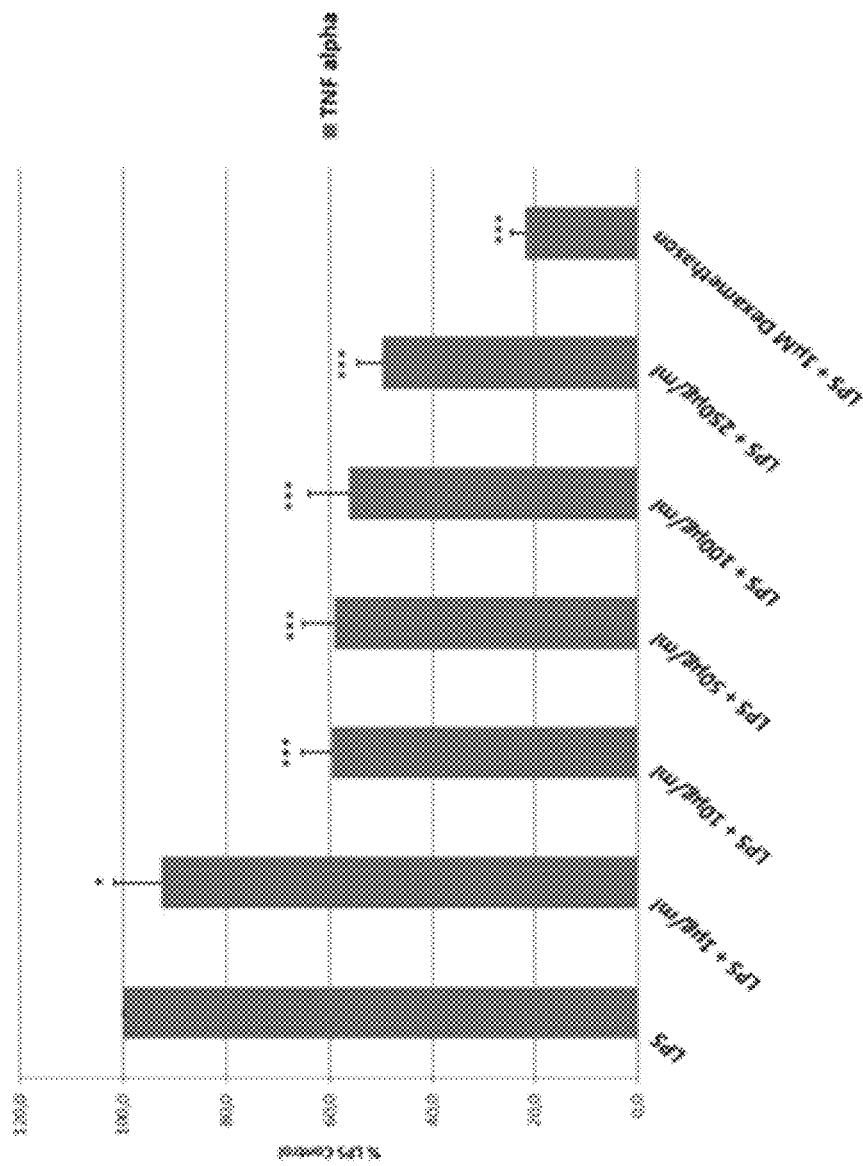
FIG. 3 is a graph depicting exemplary results for the effects of a representative composition on TNF-alpha release in primary human monocytes.
Figure 4:
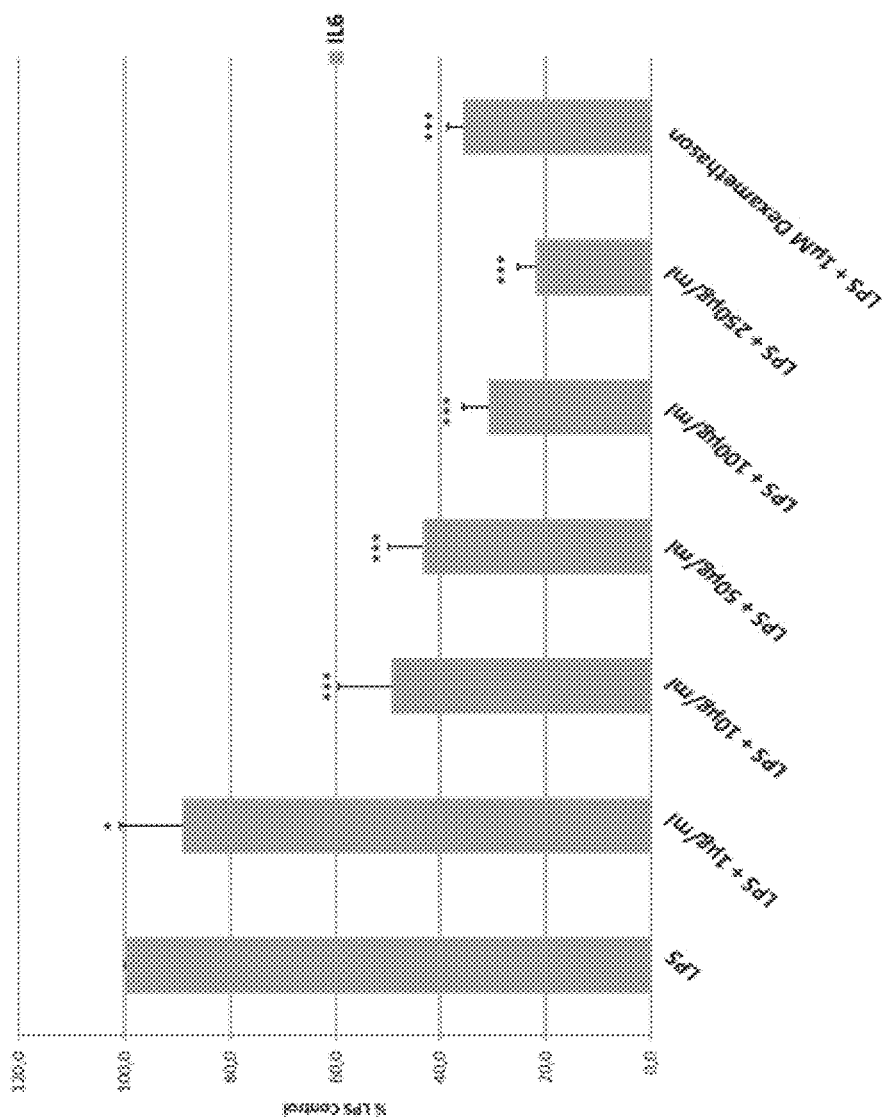
FIG. 4 is a graph depicting exemplary results for the effects of a representative composition on IL-6 release in primary human monocytes.
Figure 5:
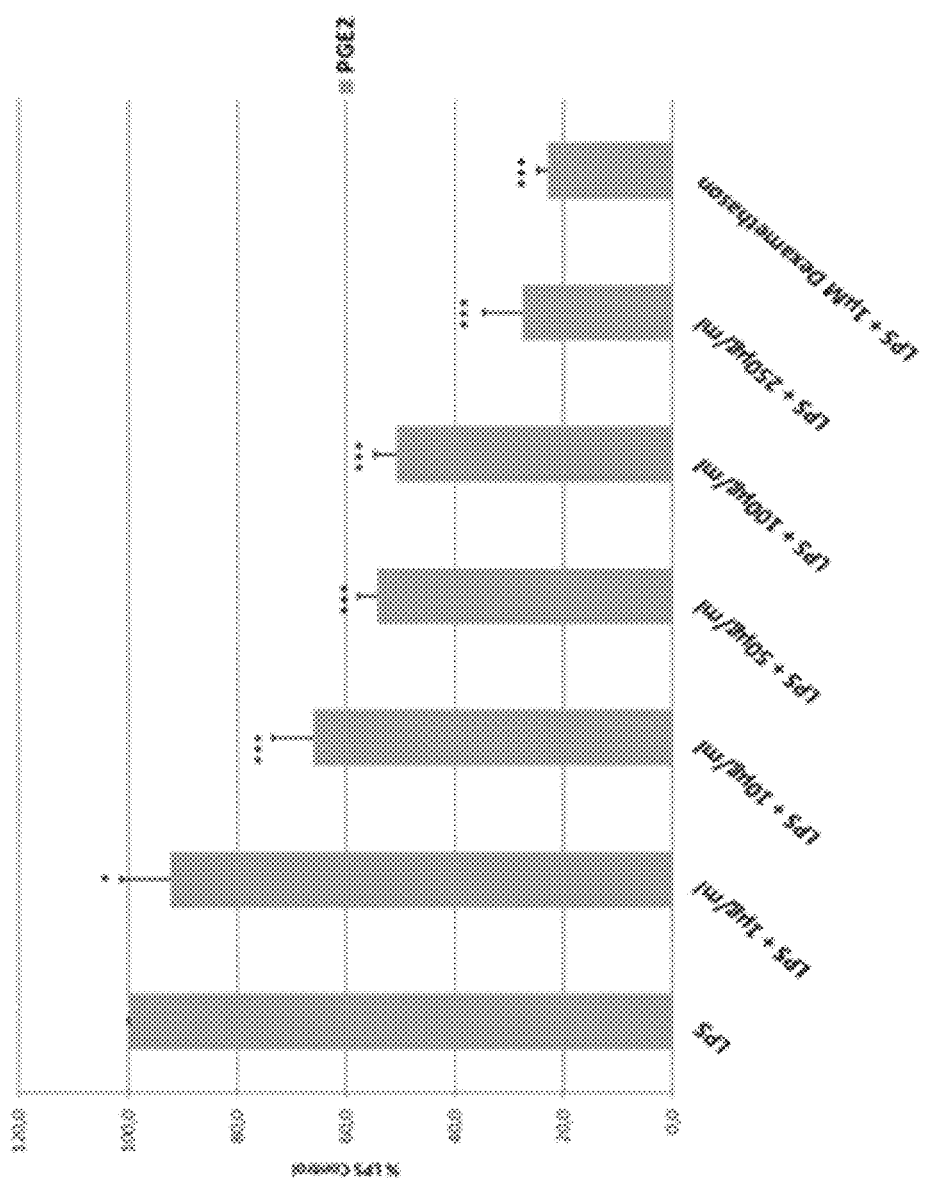
FIG. 5 is a graph depicting exemplary results for the effects of a representative composition on $PGE_2$ release in primary human monocytes.
Figure 6:
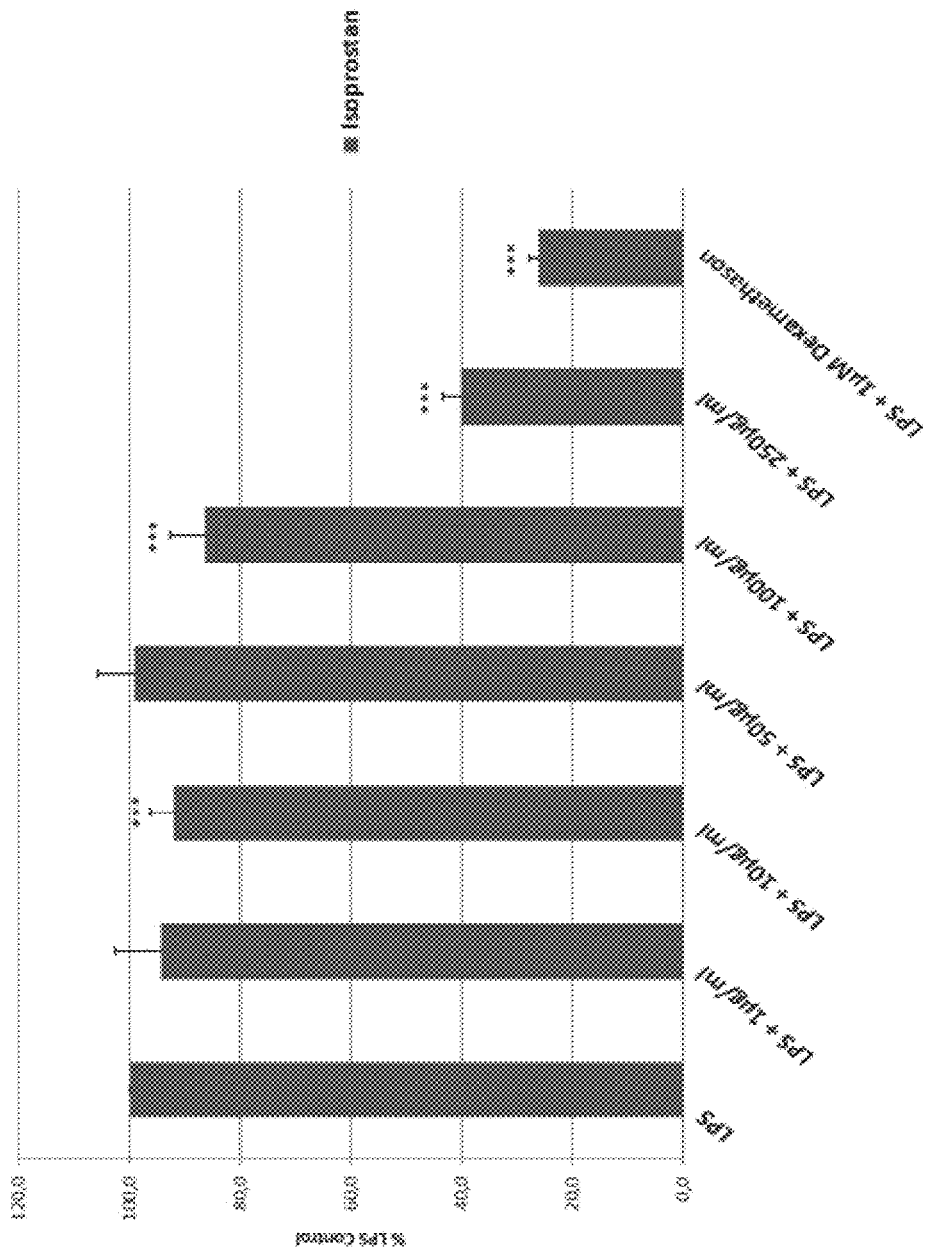
FIG. 6 is a graph depicting exemplary results for the effects of a representative composition on isoprostane release in primary human monocytes.

As can be taken for the data shown in FIGS. 1-7, the representative composition had significant effects on a variety of pro-inflammatory markers in LPS-treated primary human monocytes. As shown in the overview of FIG. 1, the representative composition potently and significantly inhibited LPS-induced IL-6, TNF-alpha, and PGE2 release starting in the low dose of 10 µg/ml. LPS-induced isoprostane (PGF2-alpha) release, a free radical marker, was inhibited in the higher doses of the extract. LPS-induced IL-23 release was not affected, whereas the levels of IL-8 and MCP1 were slightly increased. LPS-mediated IL-1beta release was enhanced by the composition. The anti-inflammatory drug and positive control dexamethasone potently prevented all parameters besides IL-23. FIG. 2 shows the inhibitory effects of the representative composition on various LPS-induced pro-inflammatory cytokines in primary human monocytes ($*p<0.05$, $p<0.01$ and $*p<0.001$ with respect to LPS control (T-test)). More particularly, FIG. 3 shows inhibitory effects of the representative composition on LPS-induced TNF-alpha release in primary human monocytes ($*p<0.05$, $p<0.01$ and $*p<0.001$ with respect to LPS control (T-test)) FIG. 4 shows inhibitory effects of the representative composition on LPS-induced IL-6 release in primary human monocytes (*p<0.05, p<0.01 and *p<0.001 with respect to LPS control (T-test)) FIG. 5 shows inhibitory effects of the representative composition on LPS-induced PGE2 release in primary human monocytes (*p<0.05, p<0.01 and *<0.001 with respect to LPS control (T-test)). FIG. 6 shows inhibitory effects of the representative composition on LPS-induced isoprostane release in primary human monocytes (*p<0.05, p<0.01 and *p<0.001 with respect to LPS control (T-test)).

Figure 7:
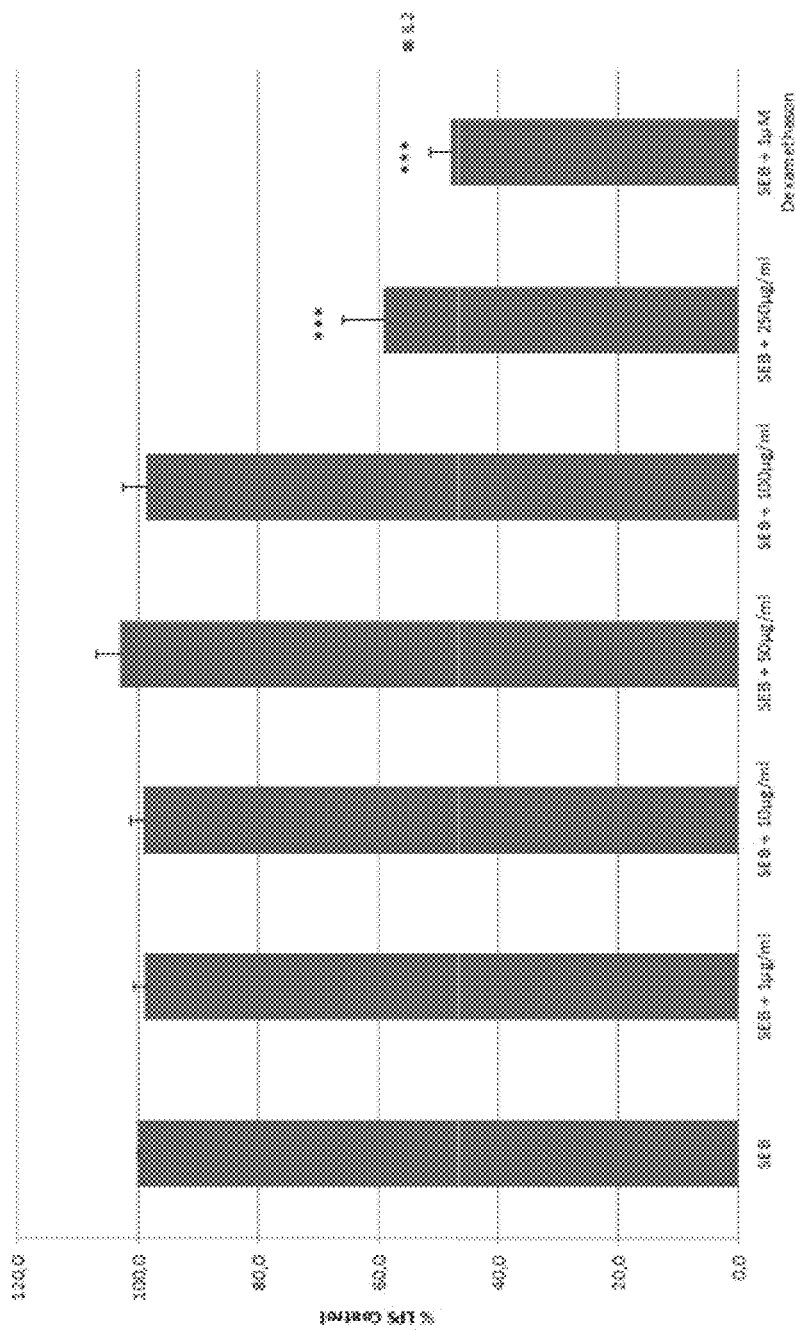
FIG. 7 is a graph depicting exemplary results for the effects of a representative composition on IL-2 synthesis in primary human lymphocytes.

As can be further taken from the data in FIG. 7, the representative composition had also significant effects on IL-2 synthesis in SEB-treated primary human monocytes (primary human T-cells). Here, the representative composition significantly inhibited LPS-induced IL-2 at higher doses (e.g., 250 µg/ml). The anti-inflammatory drug and positive control dexamethasone potently prevented IL-2 synthesis in an experimental process as described above. FIG. 7 depicts the inhibitory effects of the representative composition on SEB-induced L-2 release in primary human lymphocytes (*p<0.05, p<0.01 and *p<0.001 with respect to SEB control (T-test)). Notably, it should be appreciated that the representative compositions were effective in blunting or reducing pro-inflammatory signaling while only moderately or not at all reducing T-cell stimulation (that is commonly required for antigen-specific immune reactions).

Figure 8:
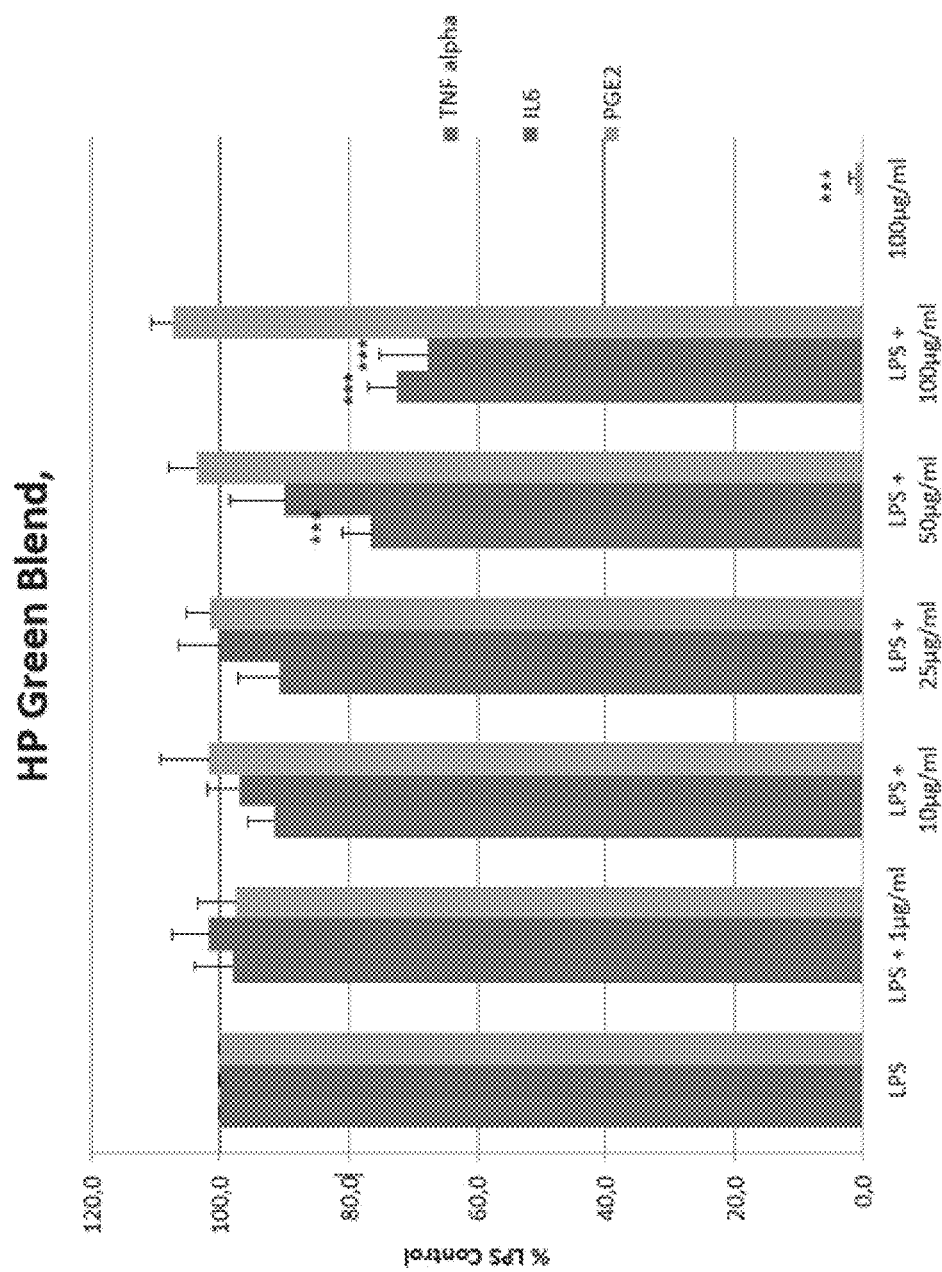
FIG. 8 is a graph depicting exemplary results for the effects of a green sub-blend of the representative composition on selected cytokines in primary human monocytes.
Figure 9:
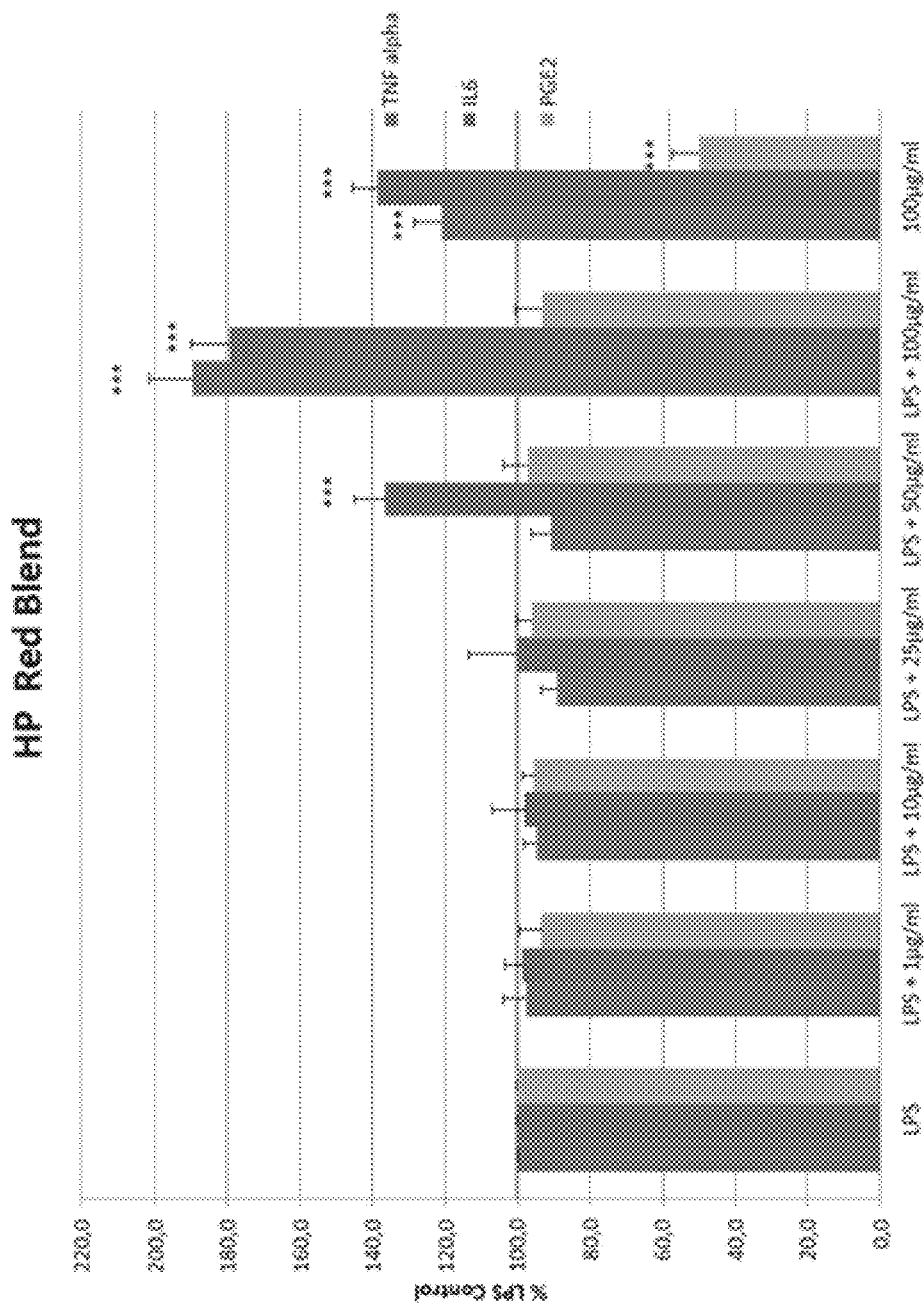
FIG. 9 is a graph depicting exemplary results for the effects of a red sub-blend of the representative composition on selected cytokines in primary human monocytes.
Figure 10:
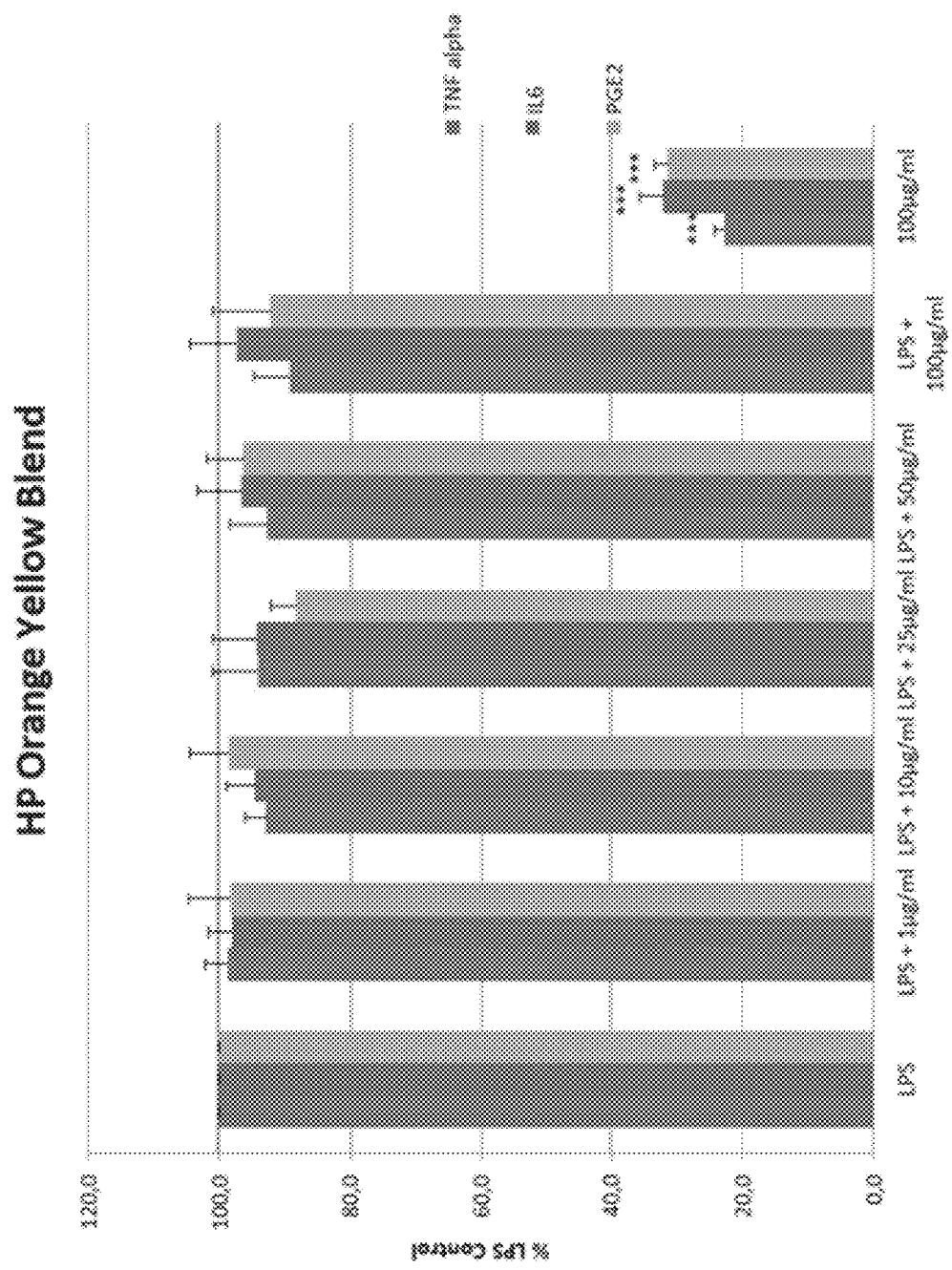
FIG. 10 is a graph depicting exemplary results for the effects of an orange/yellow sub-blend of the representative composition on selected cytokines in primary human monocytes.
Figure 11:
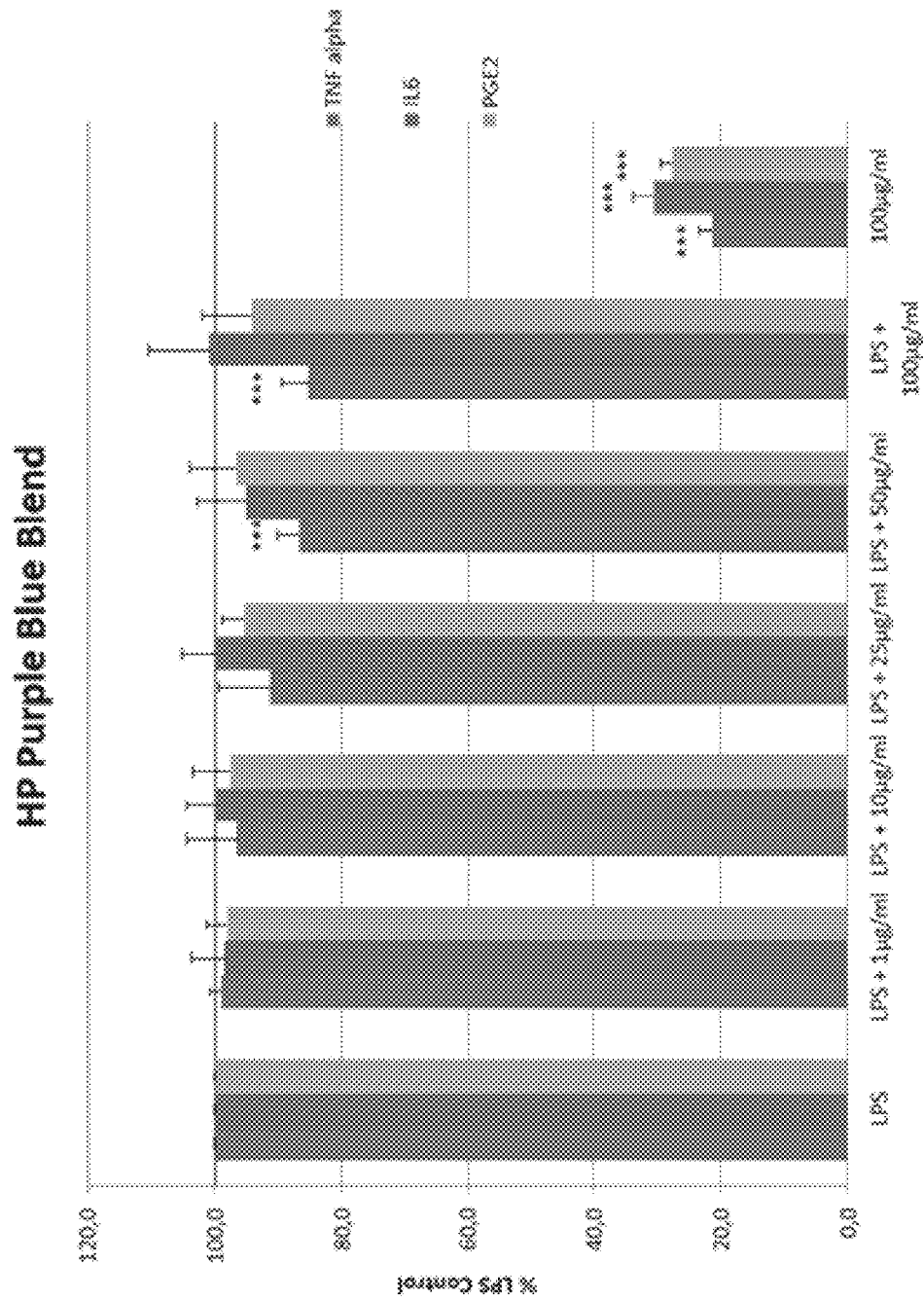
FIG. 11 is a graph depicting exemplary results for the effects of a purple/blue sub-blend of the representative composition on selected cytokines in primary human monocytes.

To investigate any potential active fractions in the representative composition, the inventor then set out to perform experiments as shown above, but only with the specific sub-blends as noted above. To that end, the inventor tested the red group sub-blend, the green group sub-blend, the orange/yellow group sub-blend, and the purple/blue group sub-blend, and typical results for TNF-alpha, IL-6, and $PGE_2$ are depicted in FIGS. 8-11 (in which *p<0.05, p<0.01 and *p<0.001 with respect to LPS control (T-test)). FIG. 8 provides a summary of the inhibition data for the green group sub-blend, FIG. 9 provides a summary of the inhibition data for the red group sub-blend, FIG. 10 provides a summary of the inhibition data for the orange/yellow group sub-blend, and FIG. 11 provides a summary of the inhibition data for the purple/blue group sub-blend.

As can be readily taken form the data in FIG. 8, the inhibition of cytokine release for TNF-alpha and IL-6 using the green sub-blend only was moderate in a dose-dependent manner, while there was no apparent PGE2 release inhibition across all tested concentrations. On the other hand, when using the red sub-blend, no significant inhibition was observed for all tested cytokines as is shown in FIG. 9. However, there was an increase in IL-6 and TNF-alpha at higher concentrations of the red sub-blend. Similarly , the orange/yellow sub-blend produced no significant inhibition or increase in all cytokines tested as can be taken from FIG. 10. There was a slight inhibition of TNF-alpha only where a purple/blue sub-blend was used as is shown in FIG. 11.

Figure 12:
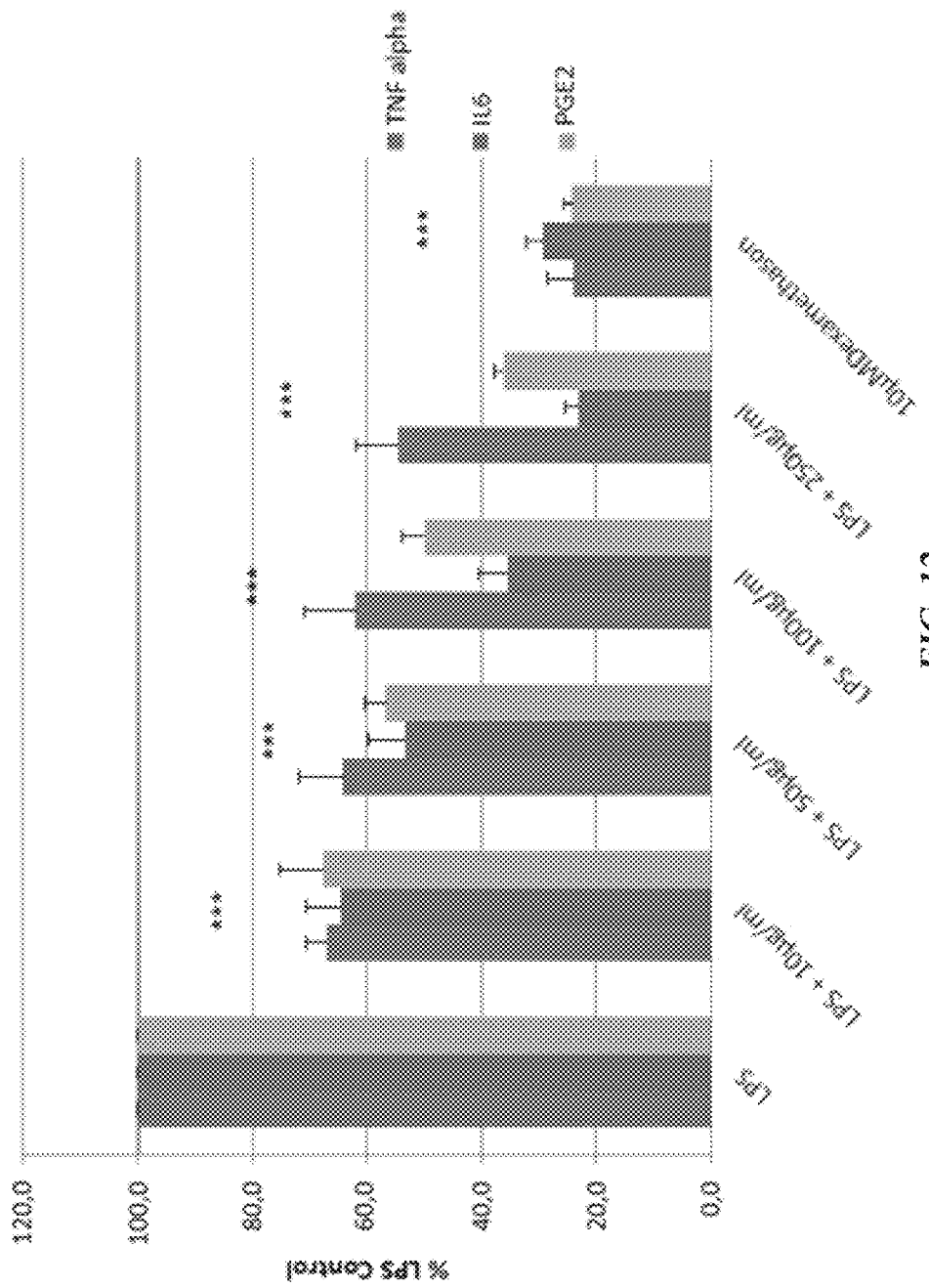
FIG. 12 is a graph depicting exemplary results for the effects of the combined sub-blends (representative composition) on selected cytokines in primary human monocytes.

Remarkably, and as can be readily seen from FIG. 12 (in which *p<0.05, p<0.01 and *p<0.001 with respect to LPS control (T-test)), when the four sub-blends were used together, a strong inhibitory synergy was observed with respect to TNF-alpha, IL-6, and $PGE_2$. Such synergistic properties were not only unexpected, but also strongly suggest that the synergistic combination is effective to reduce signs and symptoms of various inflammatory conditions (e.g., subacute, chronic, disease associated, allergy associated, etc.) across multiple and distinct pro-inflammatory pathways. Such multi-pathway inhibition is contemplated to be a significantly more effective and physiologically better tolerated anti-inflammatory immune modulation than conventional anti-inflammatory drugs. Moreover, as all of the components in the representative composition are derived from food items, a reduction of inflammation in numerous conditions (due to targeting multiple distinct pathways) can be achieved in a beneficial manner without side effects that are otherwise common with conventional anti-inflammatory drugs.

To investigate if the representative composition would also have effect on other tissues (e.g., muscle cells), the inventor determined mRNA expression for IL-6 and TNF-alpha in murine C2Cl2 muscle cells (an immortalized mouse myoblast cell line). C2Cl2 cells were provided from the University of Cordoba, Cordoba, Spain. Cells were maintained in cultures in Dulbecco's Modified Eagle's Media containing 10% Fetal Bovine Serum (FBS), 4,5 mM L-glutamine, containing 1% penicillin and streptomycin antibiotics. For all experiments, the cells were grown to 80-90% confluence in 24-well plates.

RNA isolation and quantitative PCR: Cultured cells were incubated with various concentrations of the representative composition dissolved in water (1-100 µg/ml) for 4 h. Total RNA was extracted using Universal RNA Kit—roboklon. The cDNA synthesis was reverse transcribed from 1 µg of total RNA using Moloney Murine Leukemia Virus (M-MLV) reverse transcriptase (Promega, Mannheim, Germany), RNase Inhibitor rRNasin® (Promega, Mannheim, Germany), dNTP master mix (Promega, Mannheim, Germany), and random hexamer primers (Biomers, Germany). The real-time PCR amplification was carried out by the qTOWER 2.0/2.2 Quantitative Real-Time PCR Thermal Cyclers, Analytik Jena using ORA™ qPCR Green ROX H Mix, 2×—highQu GmbH (Kraichtal, Germany). Reaction conditions were 3 mm at 95° C., followed by 40 cycles of 15 s at 95° C., 30 s at 50° C., and 45 s at 72° C., and every cycle was followed by plate reading. After that, 1 mm at 95° C., 1 min at 55° C., followed by melt curve conditions of 65° C., 95° C. with increment of 0.5° C. for 5 s, followed by final plate reading. Glyceraldehyde 3-phosphate dehydrogenase (GAPDH) served as an internal control for sample normalization, and the comparative cycle threshold Ct method was used for data quantification.

Figure 13:
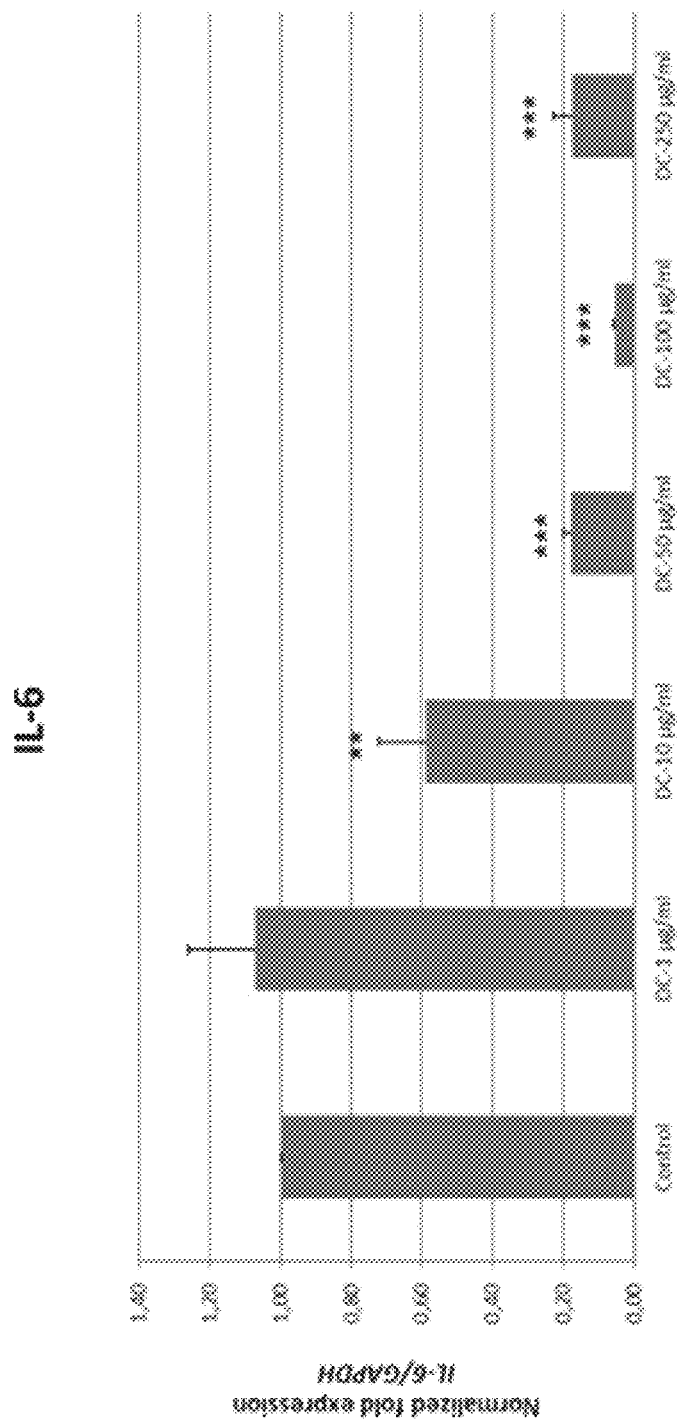
FIG. 13 is a graph depicting exemplary results for the effects of the representative composition on mRNA expression for IL-6 in C2Cl2 cells.
Figure 14:
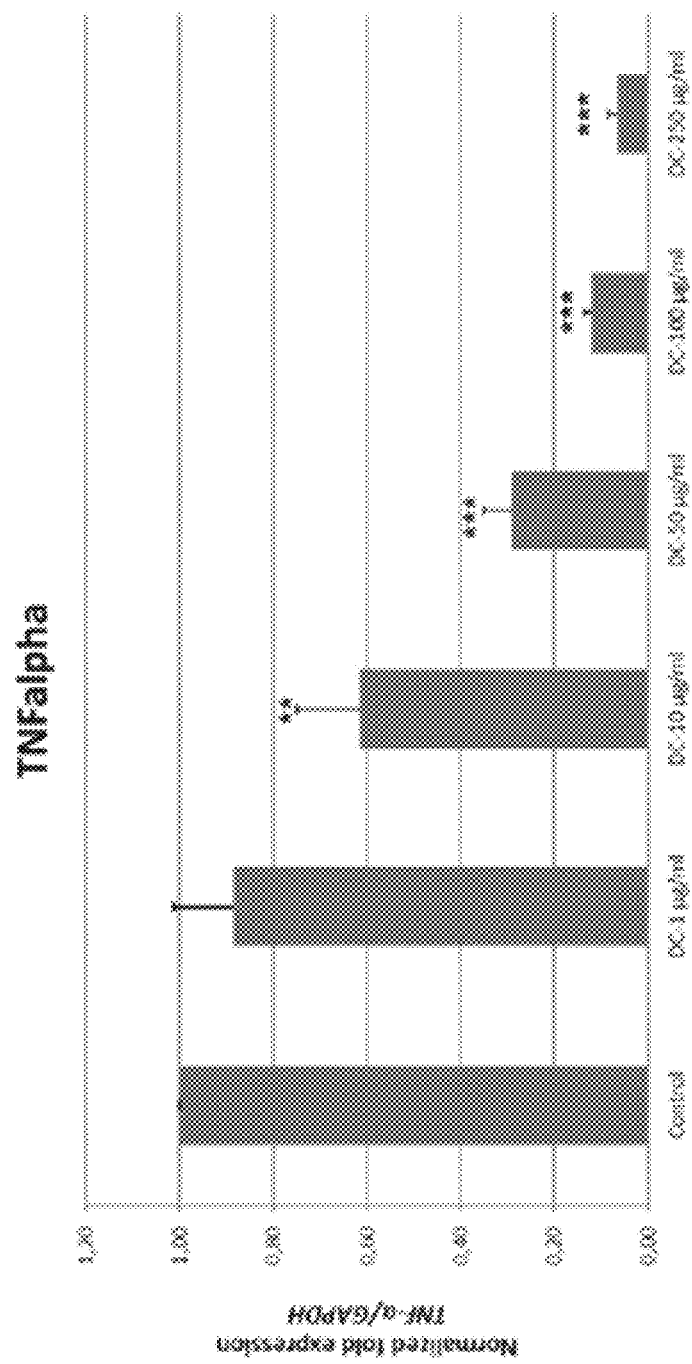
FIG. 14 is a graph depicting exemplary results for the effects of the representative composition on mRNA expression for TNF-alpha in C2Cl2 cells.

The effects of the representative compositions on IL-6 and TNF-alpha mRNA levels in C2Cl2 muscle cells is depicted in the exemplary results of FIGS. 13 and 14 (in both of which *p<0.05, **p<0.01, *p<0.001). As is readily apparent, the representative composition potently and dose-dependently decreased IL-6 and TNF-alpha mRNA levels starting with a dose of 10 µg/ml. Therefore, it should be appreciated that the representative composition has a profound effect on synthesis and secretion of selected cytokines.

NFκB

In the following experiments, the inventor performed a series of experiments to determine the effect of the representative composition on NFκB as NF-κB is one of the most important regulators of pro-inflammatory gene expression. For example, synthesis of various cytokines such as TNF-α, IL-1β, IL-6, and IL-8, is mediated by NF-κB, as is the expression of cyclooxygenase 2 (Cox-2).

To determine NF-kappaB transcriptional activity, the inventor used an assay kit with HEK293t cells that express NF-κB (nuclear factor kappa-light-chain enhancer of activated B cells) and that contained the luciferase reporter gene functionally linked to upstream NF-κB genetic response elements. Thus, quantifying changes in luciferase expression provides a sensitive surrogate measure of changes in the level of NF-κB activation. NF-κB is a signal transduction dependent transcription factor. This NF-κB reporter cell line was validated to provide a robust dose-dependent activation response when treated with TNFα, or the Protein Kinase C activator Phorbol 12-myristate 13-acetate (PMA). As such, this assay is especially suitable for screening of test samples to quantify any functional activities that they may induce or suppress NF-κB activities. Here, the NF-kappaB transcriptional activity assay was performed according to the manufacturers instructions (commercially available assay from INDIGO Biosciences (Biomol)).

Figure 15:
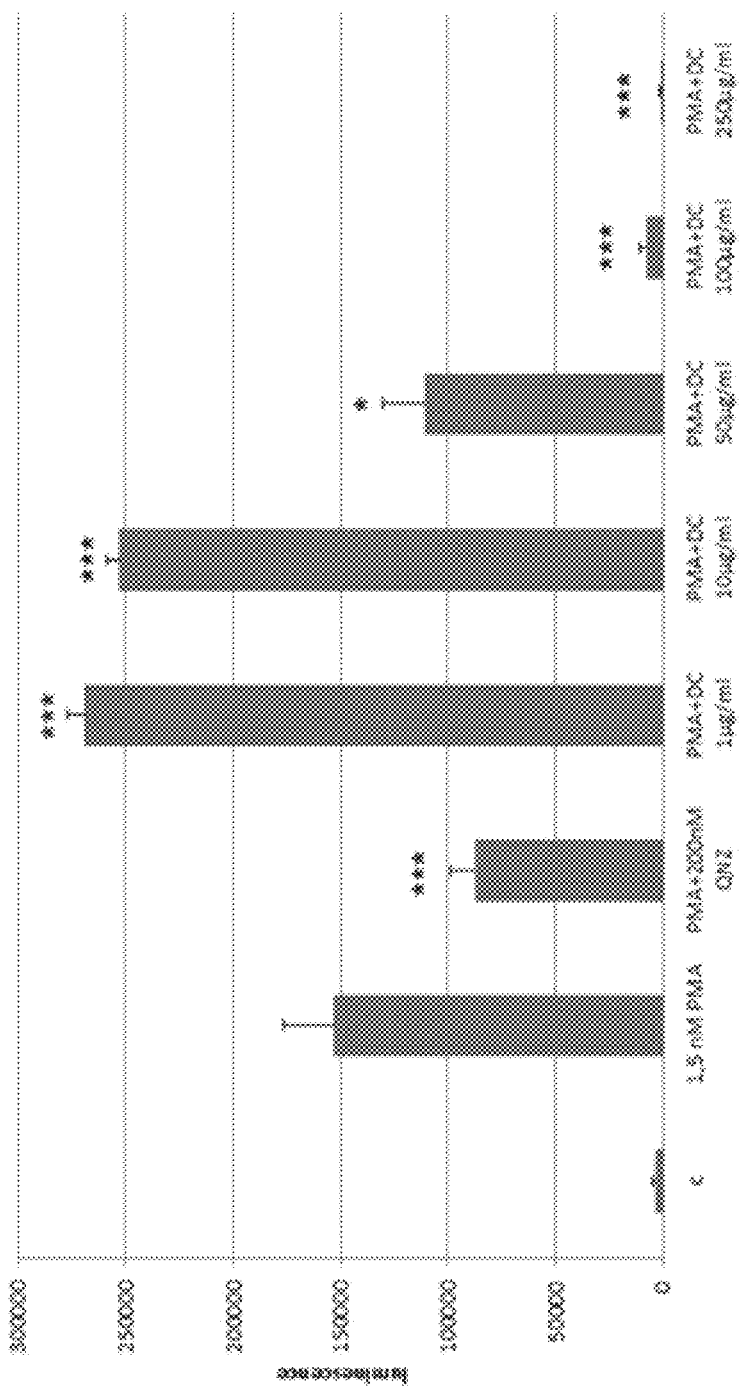
FIG. 15 is a graph depicting exemplary results for the effects of the representative composition on NFκB expression in a HEK293 model system.

Effects of the representative composition were observed using the assay as described above. As is clearly evident from the data in FIG. 15 (*$p<0.05$, **$p<0.01$, *$p<0.001$.), PMA-induced activation of NF-kappaB is enhanced at the low doses (1 and 10 µg/ml, possibly an artifact of the test system), whereas higher doses, strongly and dose-dependently prevented the activation of NF-kappaB starting with the dose of 50 µg/ml and almost complete inhibition using 100 and 250 µg/ml of the extract. Notably, such inhibition was were more potent than the known NF-kappaB inhibitor QNZ. This NF-kappaB inhibition was also consistent with the observed inhibition across various pro-inflammatory cytokines and pathways as shown above.

Glucose Uptake

In the following experiments, the inventor performed a series of assays to determine the effect of the representative composition on energy metabolism, and particularly on glucose intake.

To that end, C2Cl2 cells ($5 \times 10^4$) were seeded in 96-well black plates and incubated for 24 h. Then, medium was removed, and the cells were cultivated in OptiMEM, labeled with 50 µM 2-NBDG (2-[N-(7-nitrobenz-2-oxa-1,3-diazal-4-yl)amino]-2-deoxy-D-glucose and treated with the representative compositions or positive control Rosiglitazone for 24 h. Medium was removed and the wells were carefully washed with PBS and incubated in PBS (100 µl/well). Finally, the fluorescence was measured according to the manufacturer's instructions.

Figure 16:
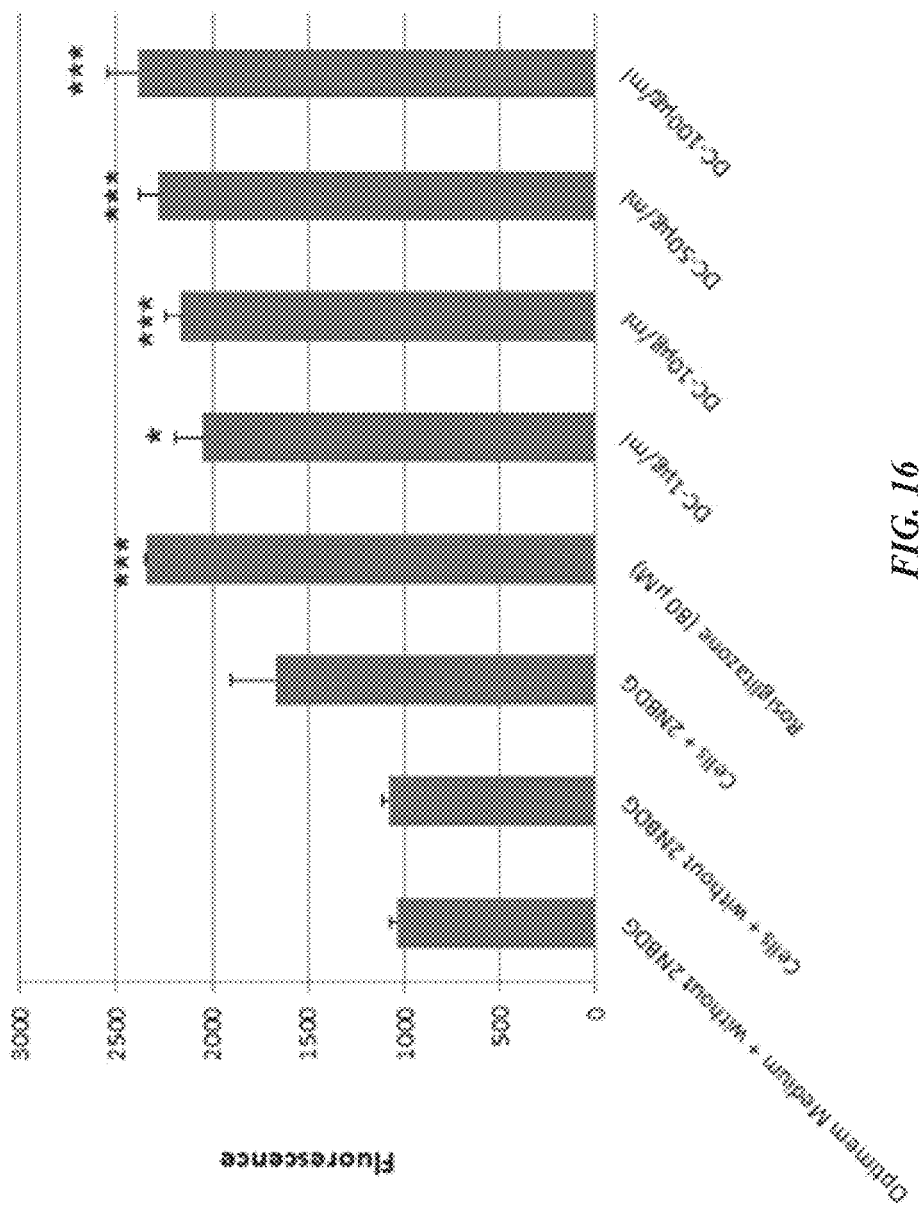
FIG. 16 is a graph depicting exemplary results for the effects of the representative composition on glucose uptake into C2Cl2 muscle cells.

FIG. 16 shows exemplary results for the effects of the representative compositions on glucose uptake in mouse C2Cl2 muscle cells (*$p<0.05$, **$p<0.01$, *$p<0.001$). As can be readily seen from the data in the graph, the effect of the representative composition on glucose uptake was remarkably high and indeed had comparable potency as the known anti-diabetic compound rosiglitazone. As such it should be appreciated that the representative composition had a significant anti-diabetic therapeutic effect and substantially promoted cellular energy.

Mitochondrial Biogenesis

Given the significant increase in available energy substrates, the inventor performed a series of experiments to investigate whether or not the increased energy metabolites could be effectively utilized in glycolysis and cellular respiration. As cellular respiration requires mitochondrial activity, the inventor sought to determine the effect of the representative composition on mitochondrial biogenesis in neuronal cells.

To that end, Neuro-2a (N2a) (ATCC, Manassas, Va., USA), cells were cultured in DMEM supplemented with 10% FBS, 2 mM l-glutamine and 1% (v/v) penicillin/streptomycin. Cells were maintained at 37° C. in a humidified atmosphere containing 5% CO2.

Determination of mitochondrial biogenesis. N2a cells were seeded in 96-well plates ($3.5 \times 10^3$ cells per well), and after 24 h, stimulated in triplicated wells with increasing concentrations of the representative composition (5 doses) for 72 h. Then, Mitotracker Green (100 nM; Thermo Fisher Scientific, Waltham, Mass., USA.) was added to culture medium for 30 min. Cells were washed with PBS, and fresh culture medium added. Images were taken and fluorescence was measured using the cell imaging system IncuCyte HD (Essen BioScience, Inc., Hertfordshire, UK). Rosiglitazone was used as a positive control.

Figure 17:
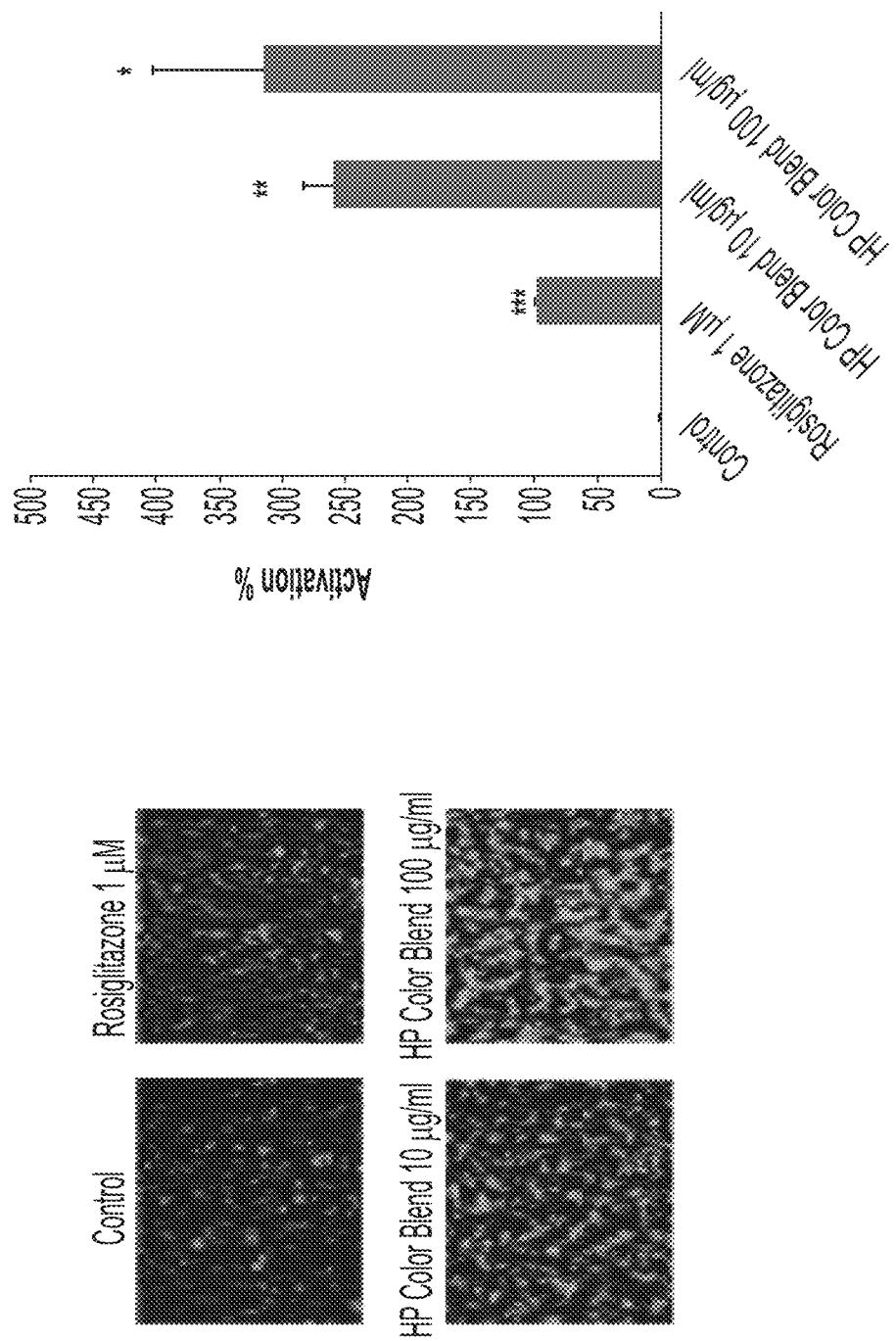
FIG. 17 is a graph depicting exemplary results for the effects of the representative composition on mitochondrial biogenesis.

As can be readily seen from the results in FIG. 17, the representative composition significantly increased mitochondrial biogenesis. Unexpectedly, the mitochondrial biogenesis using the representative composition outperformed rosiglitazone, the positive control in this assay.

ATP

In the following experiments, the inventor performed a series of tests to determine the effect of the representative composition on intracellular ATP levels. To that end, the inventor used RAW 264.1 mouse macrophages and C2Cl2 mouse muscle cells (from the Uniklinik Freiburg, Germany).

The cells were maintained in supplemented DMEM medium containing 10% FBS and 1% antibiotics penicillin/streptomycin (DMEM complete medium) at 37° C. in a humidified atmosphere of 5% CO2. For the ATP assay, the RAW Cells and C2Cl2 were seeded at a density of $2 \times 10^4$ cells/well in 96-well plates and incubated overnight in DMEM medium at 37° C. in a humidified atmosphere of 5% CO2. Then, cell cultures were stimulated with the representative compositions in selected concentrations (5 doses, n=4). ATP in the cells was determined by CellTiter-Glo® 2.0 Cell Viability/ATP Assay.

Figure 18:
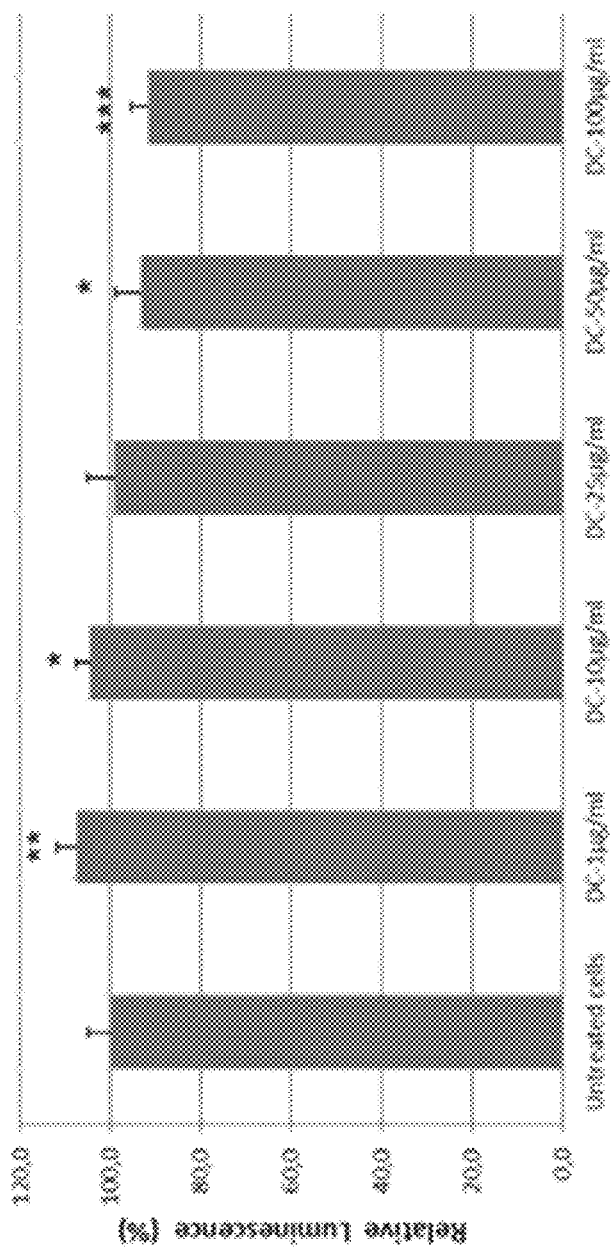
FIG. 18 is a graph depicting exemplary results for the effects of the representative composition on ATP levels in mouse RAW 264.1 macrophages.
Figure 19:
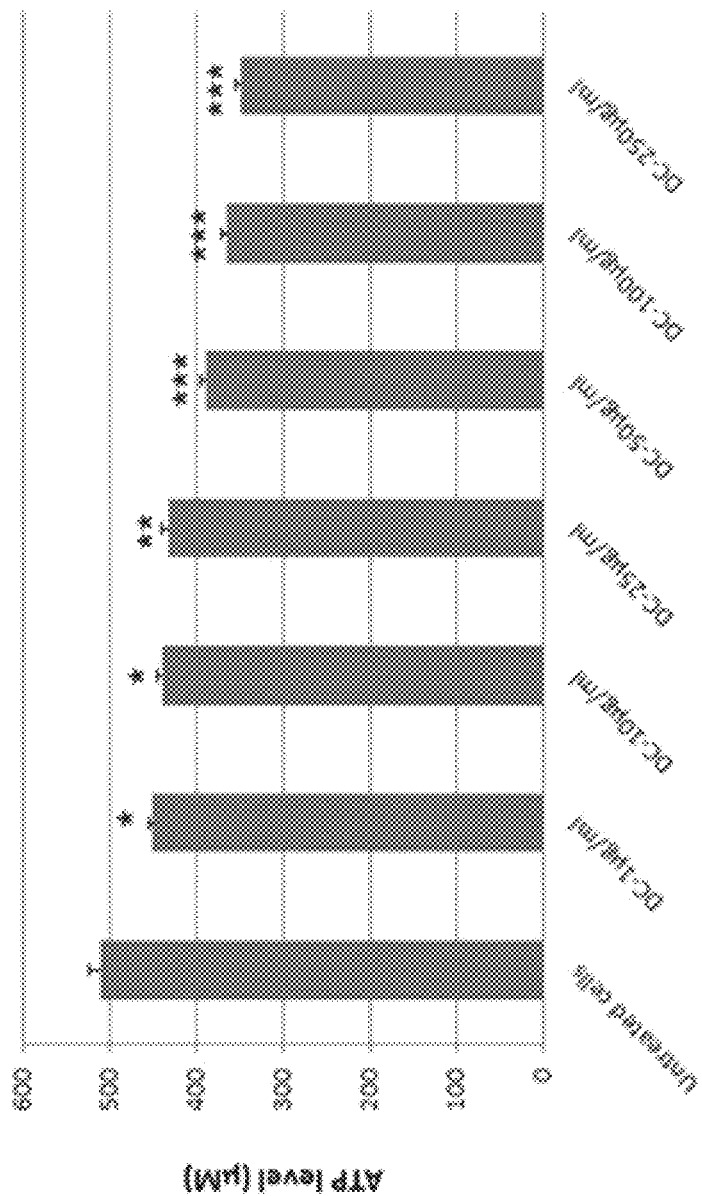
FIG. 19 is a graph depicting exemplary results for the effects of the representative composition on ATP levels in mouse C2Cl2 muscle cells.
Figure 20:
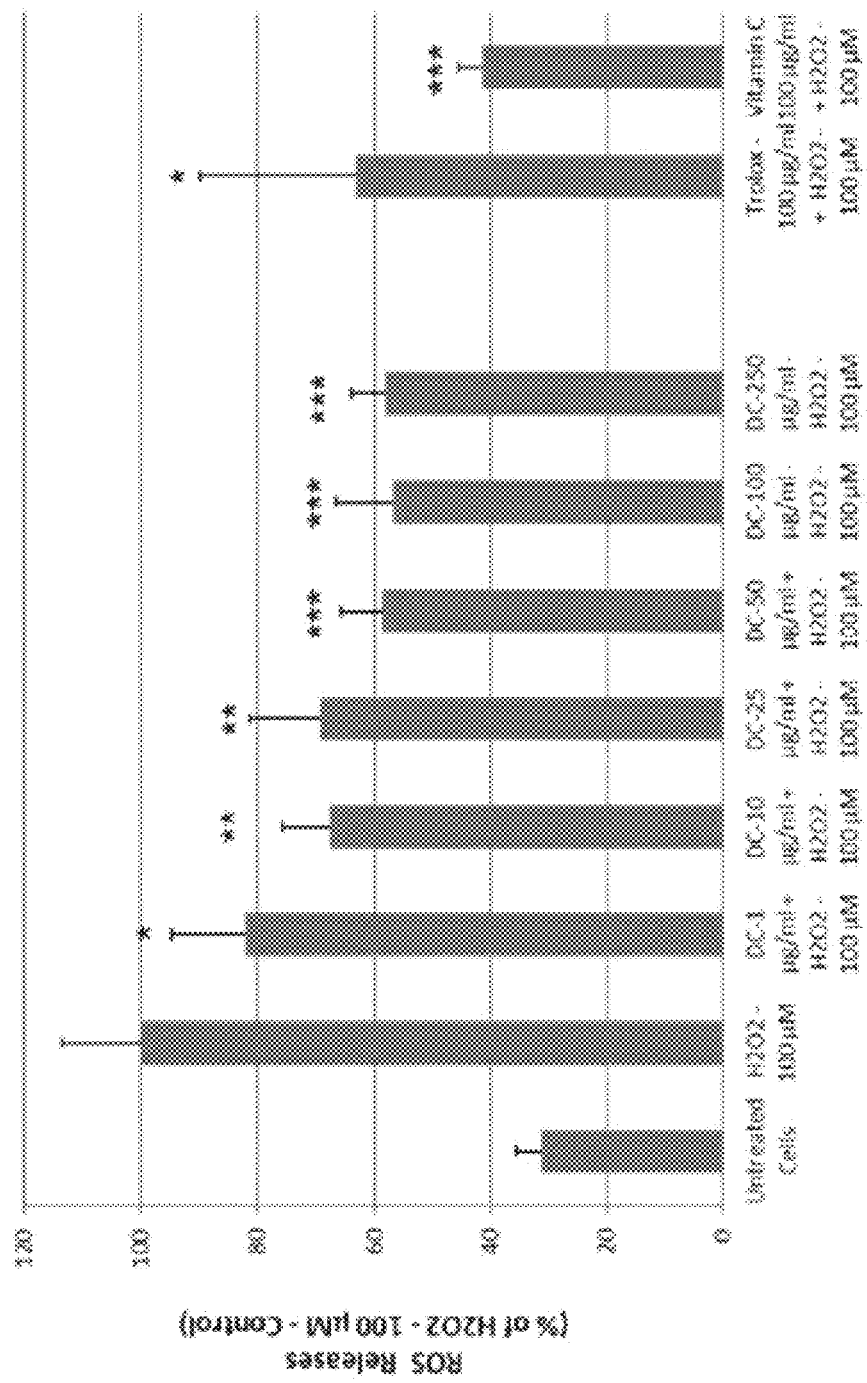
FIG. 20 is a graph depicting exemplary results for the effects of the representative composition on reactive oxygen species (ROS) in murine macrophages.

Notably, in macrophages, only the low dose of 1 µg/ml of the representative composition revealed a moderate increasing effect on ATP levels as can be seen in FIG. 18 (in which *$p<0.05$, **$p<0.01$, *$p<0.001$). All other doses were not effective. In C2Cl2 cells, the representative compositions weakly but dose-dependently inhibited ATP levels (see FIG. 19 in which *$p<0.05$, **$p<0.01$, *$p<0.001$).

Reactive Oxygen Species (ROS)

In the following experiments, the inventor performed a series of experiments to determine the effect of the representative composition on cellular antioxidant capacity by determination of reactive oxygen species (ROS) in a macrophage model system.

To that end, the inventor used RAW 264.1 mouse macrophages from the Uniklinik Freiburg, Germany. The cells were maintained in supplemented DMEM medium containing 10% FBS and 1% antibiotics penicillin/streptomycin (DMEM complete medium) at 37° C. in a humidified atmosphere of 5% $CO_2$. The cellular reaction was studied in the presence of the representative composition and controls (no compound as negative control, and Trolox and Vitamin C as positive controls). As can be clearly taken from the results in FIG. 19, $H_2O_2$-induced activation of ROS levels were potently reduced by the representative composition starting at a relatively low dose of 1 µg/ml. Remarkably, maximal ROS inhibition was achieved using 50 µg/ml of DC, which revealed a potency comparable to one of the most potent and commonly used antioxidants, Trolox C.

Adipokines

In the following experiments, the inventor performed a series of experiments to determine the effect of the representative composition on various adipokines that are associated with obesity and metabolic diseases. More specifically, the inventor used 3T3-L1 cells (preadipocyte fibroblasts) in a standard cell culture model and employed a proteome profiler kit to determine expression levels of an extended set of adipokines.

Low passage number 3T3-L1 cells (ATCC) were cultured in DMEM which contained 25 mM glucose, 4 mM L-glutamine and 1 mM sodium pyruvate supplemented with 10% (v/v) fetal bovine serum (referred to as DMEM/FBS). Cells were cultured in 12-well plates in a humidified incubator at 37° C. supplemented with 5% (v/v) CD2. Two days post-confluence, differentiation to adipocytes was induced with a cocktail of stimulants; 2 µg/mL insulin, 0.5 mM isobutyl-methylxanthine, 0.25 µM dexamethasone and 2 µM rosiglitrazone (all purchased from Sigma) in DMEM/FBS. After three days, the differentiation medium was removed and cells were maintained in post-differentiation medium (DMEM/FBS with 2 µg mL-1 insulin) for a further 6-9 days, with media changes every two days or as required. Differentiation was monitored daily by microscopy.

After differentiation, the cells were washed with PBS, incubated in complete DMEM medium and treated with TNFα (50 ng/ml) in the absence and presence of the representative composition (10 and 100 µg/ml, dissolved in water) for 24 h. The supernatants were collected and assayed for detection of adipokines and other related soluble mediators. Adipokines and other obesity-related proteins were detected using the semiquantitative Proteome Profiler Mouse Adipokine Array Kit (R&D System; Minneapolis, Minn., USA) according to the manufacturer's recommendations. Pixel densities on developed X-Ray films were collected with a scanner and analyzed using the ImageJ processing and analysis program (NIH; Bethesda, Md., USA).

The following adipokines and soluble mediators were monitored simultaneously: Adiponectin, AgRP, ANGPT-L3, C-Reactive Protein, DPPIV, Endocan, Fetuin A, FGF acidic, FGF-21, HGF, ICAM-1, IGF-I, IGF-II, IGFBP-1, IGFBP-2, IGFBP-3, IGFBP-5, IGFBP-6, IL-6, IL-10, IL-11, Leptin, LIF, Lipocalin-2, MCP-1, M-CSF, Oncostatin M, Pentraxin 2, Pentraxin 3, Pref-1, RAGE, RANTES, RBP4, Resistin, Serpin E1, TIMP-1, TNF-alpha, and VEGF.

Figure 21:
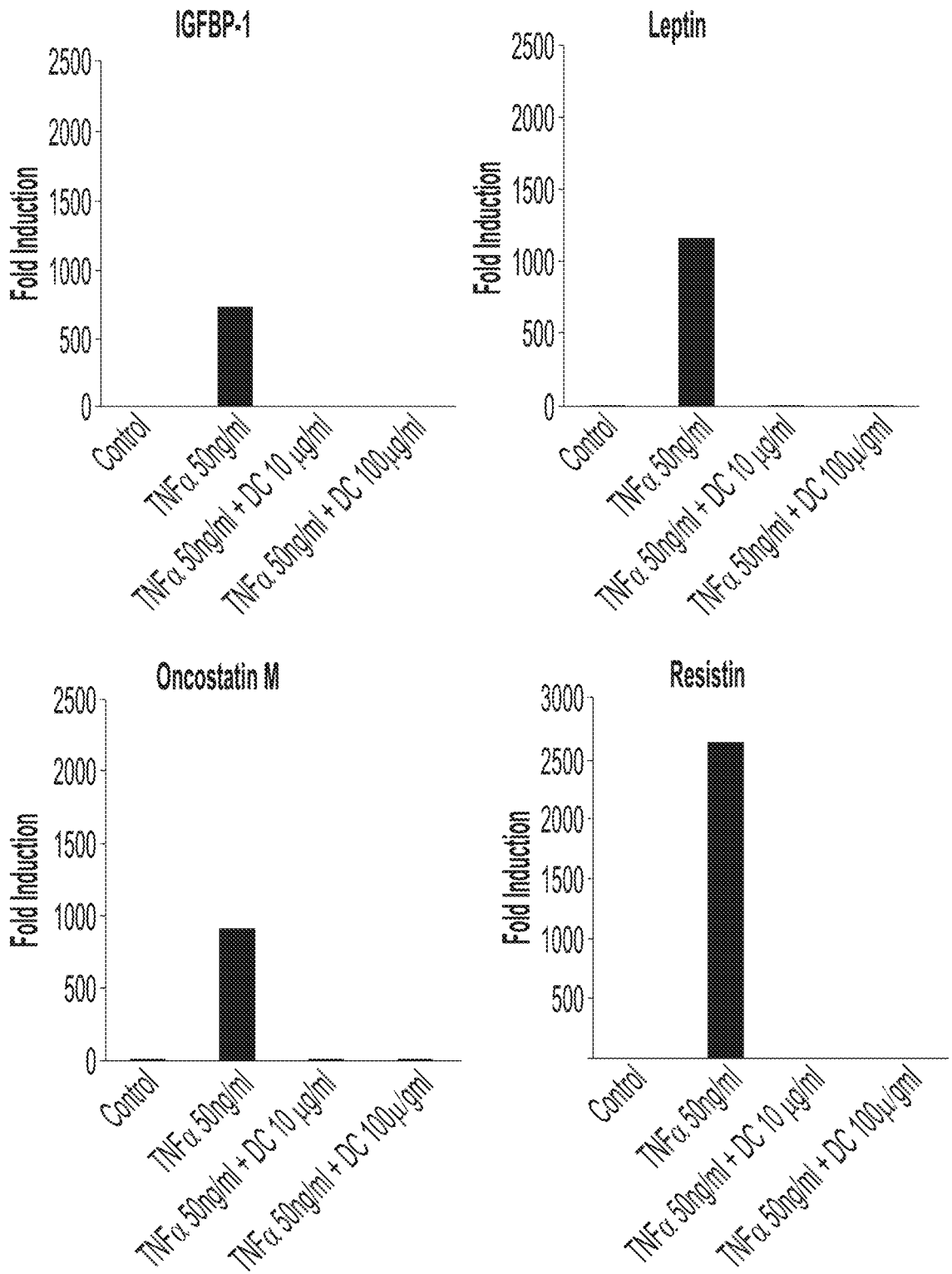
FIG. 21 is a graph depicting exemplary results for the suppressive effects of the representative composition on selected adipokinins.
Figure 22:
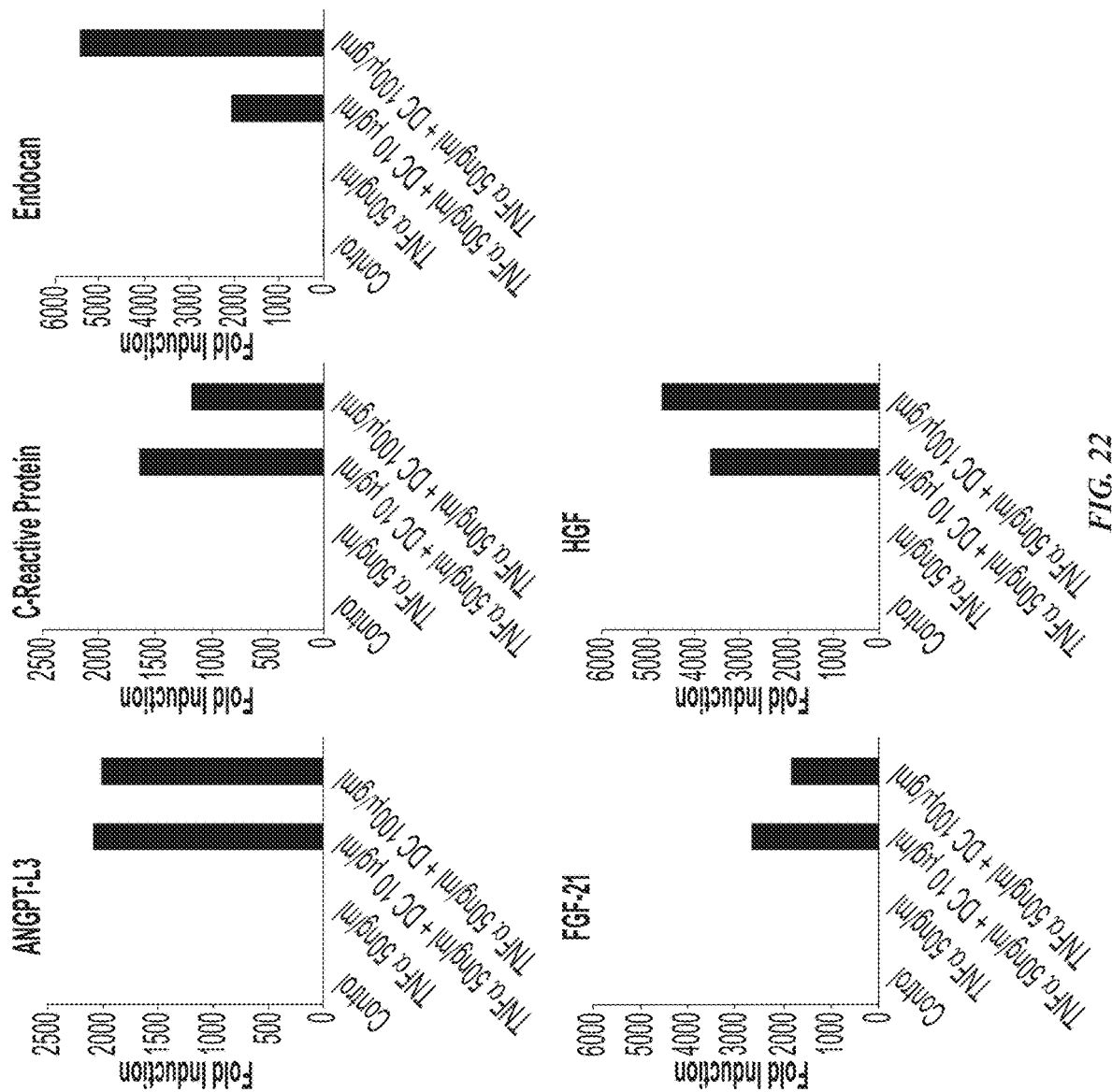
FIG. 22 is a graph depicting exemplary results for the stimulating effects of the representative composition on a first set of selected adipokinins.
Figure 23:
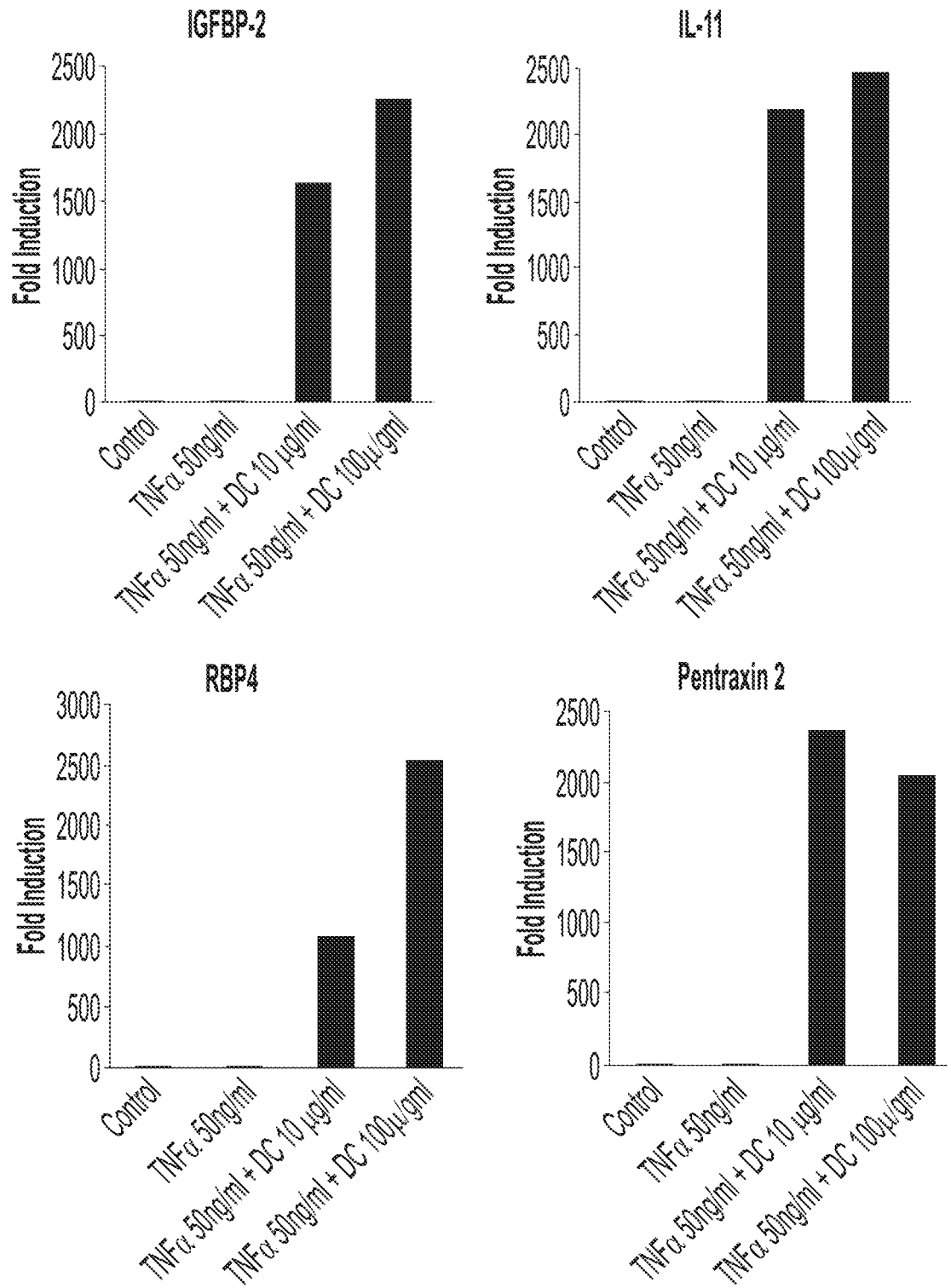
FIG. 23 is a graph depicting exemplary results for the suppressive effects of the representative composition on a second set of selected adipokinins.

FIGS. 19-22 depict selected effects of the representative composition on the secretion of obesity related proteins in differentiated 3T3-L1 cells. Most notably, TNFα induced the secretion of IGFBP-1, Leptin, Oncostatin M and Resistin, and this secretion was completely inhibited by the representative composition as can be seen in FIG. 21. In contrast, and as is shown in FIG. 22 and FIG. 23, ANGPT-L3, C-Reactive Protein, Endocan, FGF-21, HGF, IGFBP-2, IL-11, RBP4 and Pentraxin 2 were clearly induced by TNFα+representative composition but not with TNFα alone, suggesting that the synthesis of these proteins was induced by the representative composition.

Senescence

In the following experiments, the inventor performed a series of experiments to determine the effect of the representative composition on gene expression for selected senescence markers in normal human dermal fibroblasts (NHDF).

NHDF cells were purchased from (ATCC, Germany). NHDF cells were maintained in cultures in Dulbecco's Modified Eagle's Media containing 10% Fetal Bovine Serum (FBS), 4,5 mM L-glutamine, containing 1% penicillin and streptomycin antibiotics. NHDF cells were grown at 37° C. in humidified 5% CO2. For all experiments, the cells were grown to 80-90% confluence in 24-well plates. 24 h after cell culture we change the medium and we keep the NHDF cells for 6 days for senescence.

Quantitative real-time PCR (qPCR) was performed in Senescence Normal Human Dermal Fibroblasts. Cultured Senescence NHDF cells were incubated with various concentrations of the representative composition dissolved in either water (1-100 µg/ml) for 4 h. Total RNA was then extracted using Universal RNA Kit—roboklon. The cDNA synthesis was reverse transcribed from 1 µg of total RNA using Moloney Murine Leukemia Virus (M-MLV) reverse transcriptase (Promega, Mannheim, Germany), RNase Inhibitor rRNasin® (Promega, Mannheim, Germany), dNTP master mix (Promega, Mannheim, Germany), and random hexamer primers (Biomers, Germany). Real-time PCR amplification was carried out by the qTOWER 2.0/2.2 Quantitative Real-Time PCR Thermal Cyclers, Analytik Jena using ORA™ qPCR Green ROX H Mix, 2×—highQu GmbH (Kraichtal, Germany). Primers were designed to amplify genes encoding HGF, c-fos, p16$^{INK}$, and p21. Reaction conditions were 3 min at 95° C., followed by 40 cycles of 15 s at 95° C., 30 s at 50° C., and 45 s at 72° C., and every cycle was followed by plate reading. After that 1 min at 95° C., 1 mm at 55> C., followed by melt curve conditions of 65° C., 95° C. with increment of 0.5° C. for 5 s, followed by final plate reading. Glyceraldehyde 3-phosphate dehydrogenase (GAPDH) served as an internal control for sample normalization, and the comparative cycle threshold Ct method was used for data quantification.

Figure 24:
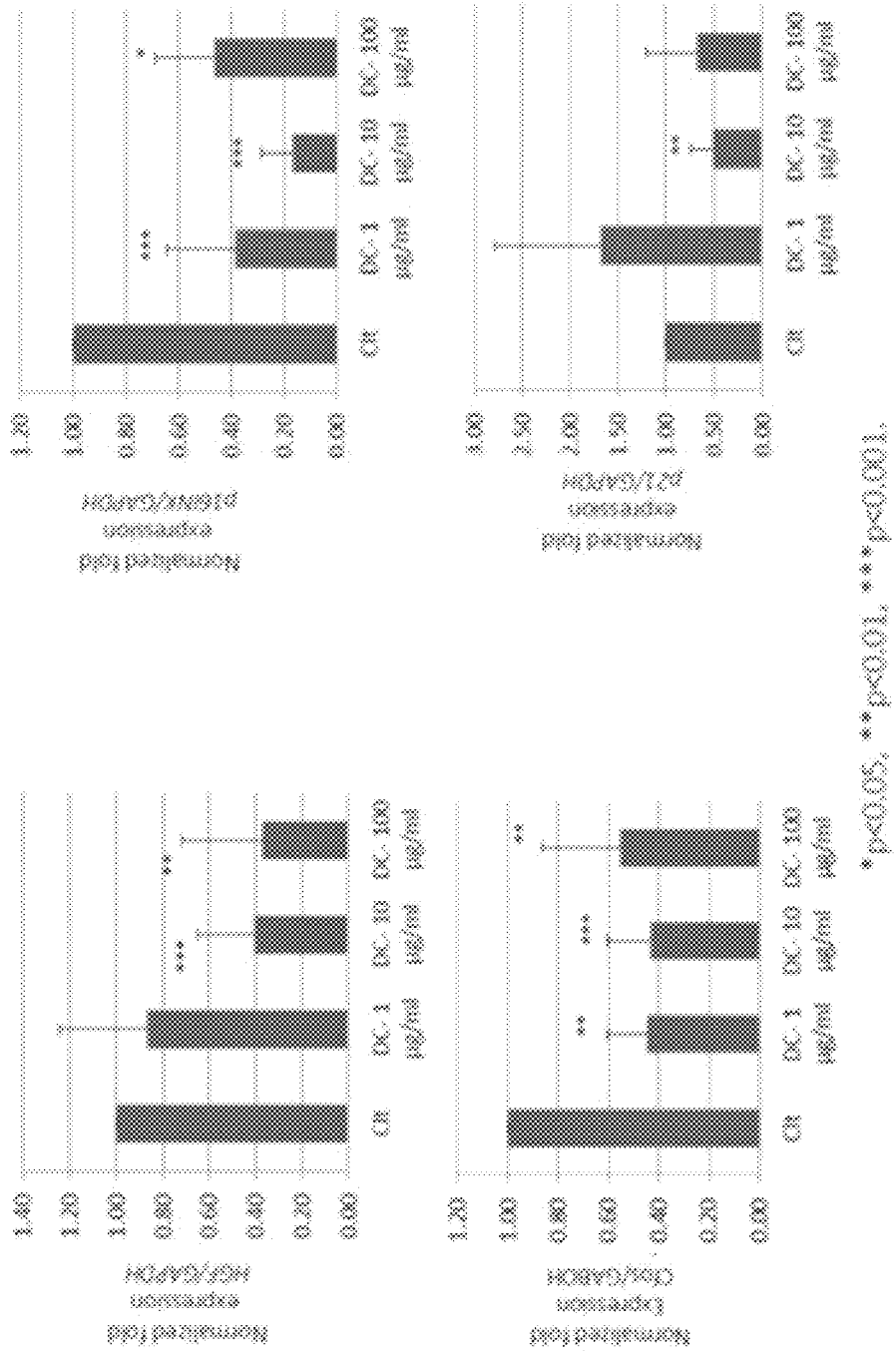
FIG. 24 is a graph depicting exemplary results for the effects of the representative composition on gene expression of selected genes associated with senescence.

Notably, and as can be seen from FIG. 24, the representative composition strongly inhibited expression of the senescence associated genes HGF, c-fos, p16$^{INK}$, and p21, even at very low dosages.

Acetylcholine Esterase (AChE)

In the following experiments, the inventor performed a series of experiments to determine the effect of the representative composition on AChE as a potential target of interest with regard to neural function.

To that end, the inventor used an Amplite™ Colorimetric assay (from AAT Bioquest) following the manufacturer's instructions. 40 µl assay buffer for the NIC (No Inhibitor Control), 40 µl of the AHE solutions and 40 µl of a diluted Donepezil stock solution in assay buffer as negative control were pipetted into separate wells of a 96 well plate. For the negative controls, NICs and test sample solutions 10 µl of an acetylcholinesterase solution (4 mU/10 µl) was added to each well. The control samples and samples with the representative composition were incubated for 15 min at room temperature with slow shaking. 50 µL of the AChE working solution was added to each well to make a total Acetylcholinesterase assay volume of 100 µl/well (t=0 min). The reaction was incubated for 60 minutes at room temperature, protected from light (t=60 min). Absorbance was measured at 405 nm with the PerkinElmer Victor X5 2030-0050 Multimode Plate Reader, PerkinElmer (Rodgau, Germany) at timepoints t=0 min and t=60 min.

Figure 25:
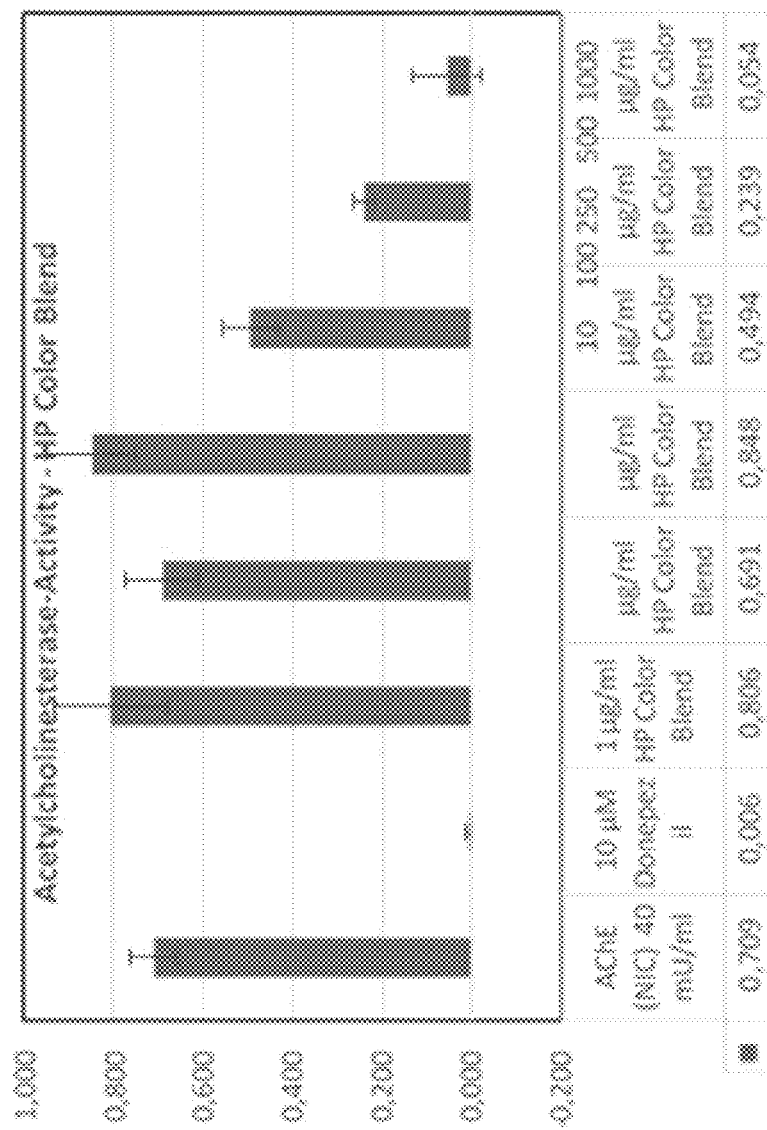
FIG. 25 is a graph depicting exemplary results for the effects of the representative composition on acetylcholine esterase activity.

Exemplary test results are shown in FIG. 25 depicting the effects of the representative composition on acetylcholinesterase activity. The results are expressed in relative units±SD (*p<0.05, **p<0.01, *p<0.001). As can be readily seen, the representative composition had significant inhibitory effect of AChE at higher concentrations.

Viability

In the following experiments, the inventor performed a series of experiments to determine the effect of the representative composition on cellular viability of macrophages. Here, the RAW 264.1 mouse macrophages were obtained from the Uniklinik Freiburg and maintained in supplemented DMEM medium containing 10% FBS and 1% antibiotics penicillin/streptomycin (DMEM complete medium) at 37° C. in a humidified atmosphere of 5% $CO_2$ following standard protocols.

Figure 26:
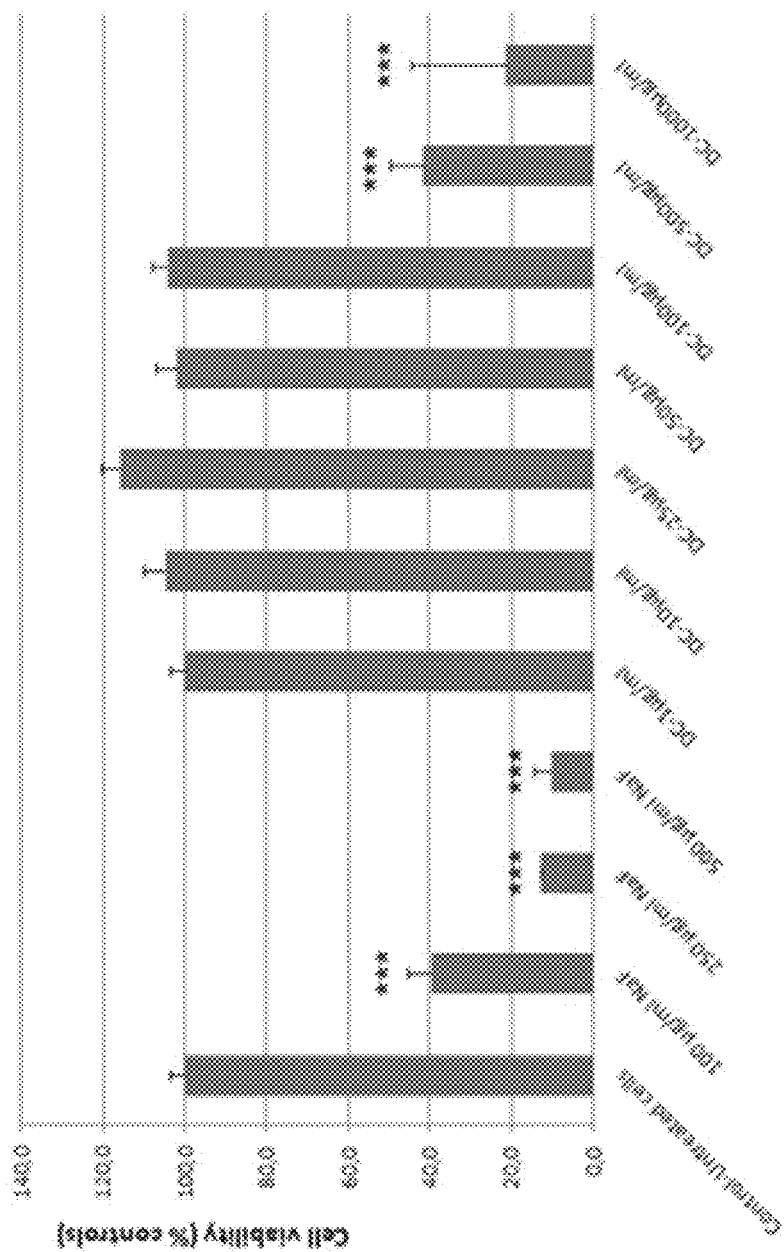
FIG. 26 is a graph depicting exemplary results for the effects of the representative composition on cellular viability and metabolism of macrophages.

The cytotoxicity assay was performed by seeding the RAW cells at a density of $2\times10^4$ cells/well in 96-well plates and incubated overnight in DMEM medium at 37° C. in a humidified atmosphere of 5% $CO_2$. Then, cell cultures were stimulated with the representative composition at selected concentrations (7 doses, n=4), and cell viability was determined by Alamar Blue staining using NaF as toxic control. Exemplary results are depicted in FIG. 26. As can be readily seen from the results, only high dosages at and above 500 μg/ml showed some effects on cell viability or cell metabolism whereas lower concentrations had no statistically significant impact on cell viability and cell metabolism.

Further aspects, considerations, and contemplations suitable for use herein are disclosed in U.S. Pat. No. 11,065,295 which is incorporated by reference herein.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical or nutraceutical composition refers to both direct and indirect administration of the pharmaceutical or nutraceutical composition, wherein direct administration of the pharmaceutical or nutraceutical composition is typically performed by a health care professional (e.g., physician, nurse, dietitian, etc.), and wherein indirect administration includes a step of providing or making available the pharmaceutical or nutraceutical composition to the health care professional or individual in need thereof for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by content. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the team "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A nutritional composition, comprising:
a nutritionally acceptable carrier in combination with a plurality of chemically distinct polyphenol-containing plant materials having a red color, a green color, an orange-yellow color, and a purple-blue color;
wherein the red colored plant materials comprise an apple extract, a pomegranate extract, a tomato powder, and a beet root powder. wherein the green colored plant materials comprise an olive extract, a rosemary extract. a green coffee bean extract, and a kale powder, wherein the orange-yellow colored plant materials comprise an onion extract, a ginger extract, a grapefruit extract, and a carrot powder, and/or wherein the purple-blue colored plant materials comprise a grape extract, a blueberry extract, a currant powder, and an elderberry powder;
wherein the combination of plant materials is a synergistic combination with respect to inhibition of pro-inflammatory cytokine release in human leukocytes.

2. The composition of claim 1, wherein the pro-inflammatory cytokine release is release of at least one of tumor necrosis factor alpha (TNF-alpha), interleukin-6 (IL-6), prostaglandin $E_2$ ($PGE_2$), and isoprostane.

3. The composition of claim 1, wherein the composition further reduces expression of NFκB.

4. The composition of claim 1, wherein the composition further increases glucose uptake into a cell and/or increases mitochondrial biogenesis in a cell.

5. The composition of claim 1, wherein the composition further reduces oxidative damage due to reactive oxygen species.

6. The composition of claim 1, wherein the composition further reduces expression of pro-inflammatory adipokines.

7. The composition of claim 1, wherein the composition further reduces expression of senescence associated genes.

8. The composition of claim 1, wherein the composition is formulated for oral administration, optionally in single dosage units.

9. The composition of claim 8, wherein the single dosage unit contains between 50 and 1,000 mg of the composition.

10. The composition of claim 8, wherein the single dosage unit is formulated as a capsule, a gummy, or a powder.

11. The composition of claim 1, further comprising a vitamin, a dietary trace element or mineral, a probiotic, and/or a prebiotic.

12. The composition of claim 1, further comprising a niacin, a niacinamide, a nicotinamide riboside, a nicotinamide mononucleotide, a nicotinamide adenine dinucleotide, and/or a nutritionally acceptable CD38 inhibitor.

13. The composition of claim 1, wherein the composition is effective to treat or reduce a symptom associated with an inflammatory condition, a metabolic dysregulation, a neurological condition, a cardiovascular condition, senescence, and/or oxidative stress.

14. A method of supporting health in a subject, comprising administering to the individual a composition according to claim 1.

15. The method of claim 14, wherein the composition is administered in an amount effective to thereby treat or reduce a symptom associated with an inflammatory condition, a metabolic dysregulation, a neurological condition, a cardiovascular condition, senescence, and/or oxidative stress.

16. The method of claim 14, wherein the composition is administered over at least 30 days and/or at a daily dose of between 50 and 1,000 mg.

17. A method of reducing inflammaging in a subject, comprising:
administering to the subject the composition of claim 1,
wherein the combination of plant materials reduce release of at least one pro-inflammatory cytokine in human cells and reduce expression of at least one senescence-associated gene in human cells.

18. The method of claim 17, wherein the pro-inflammatory cytokine is selected from the group consisting of tumor necrosis factor alpha (TNF-alpha), interleukin-6 (IL-6), prostaglandin $E_2$ ($PGE_2$), and isoprostane, wherein the red colored plant materials, the green colored plant materials, the orange-yellow colored plant materials, and the purple-blue colored plant materials are present in synergistic quantities with respect to reducing pro-inflammatory cytokine release of at least one cytokine in the human cells, and/or wherein the senescence-associated gene is selected from the group consisting of HGF, c-fos, $p16^{INK}$, and p21.

* * * * *